United States Patent
Hohn et al.

(10) Patent No.: US 11,957,755 B2
(45) Date of Patent: *Apr. 16, 2024

(54) RADIOPAQUE POLYMERS

(71) Applicant: Boston Scientific Medical Device Limited, Galway (IE)

(72) Inventors: Stephane Hohn, The Hague (NL); Andrew Lennard Lewis, Camberley (GB); Sean Leo Willis, Camberley (GB); Matthew R. Dreher, West Conshohocken, PA (US); Koorosh Ashrafi, Camberley (GB); Yiqing Tang, Camberley (GB)

(73) Assignee: Boston Scientific Medical Device Limited, Galway (IE)

( * ) Notice: Subject to any disclaimer, the term of this patent is extended or adjusted under 35 U.S.C. 154(b) by 203 days.

This patent is subject to a terminal disclaimer.

(21) Appl. No.: 17/329,891

(22) Filed: May 25, 2021

(65) Prior Publication Data

US 2021/0275674 A1 Sep. 9, 2021

Related U.S. Application Data

(63) Continuation of application No. 16/733,454, filed on Jan. 3, 2020, now Pat. No. 11,040,104, which is a continuation of application No. 16/243,672, filed on Jan. 9, 2019, now Pat. No. 10,568,967, which is a continuation of application No. 14/916,477, filed as application No. PCT/GB2014/000352 on Sep. 5, 2014, now Pat. No. 10,350,295.

(30) Foreign Application Priority Data

Sep. 6, 2013 (GB) .................... 1315923

(51) Int. Cl.
| | | |
|---|---|---|
| *A61K 9/00* | (2006.01) | |
| *A61K 31/404* | (2006.01) | |
| *A61K 31/41* | (2006.01) | |
| *A61K 31/44* | (2006.01) | |
| *A61K 31/4745* | (2006.01) | |
| *A61K 31/517* | (2006.01) | |
| *A61K 31/555* | (2006.01) | |
| *A61K 31/704* | (2006.01) | |
| *A61K 47/34* | (2017.01) | |
| *A61K 49/04* | (2006.01) | |

(52) U.S. Cl.
CPC ............ *A61K 47/34* (2013.01); *A61K 9/0024* (2013.01); *A61K 31/404* (2013.01); *A61K 31/41* (2013.01); *A61K 31/44* (2013.01); *A61K 31/4745* (2013.01); *A61K 31/517* (2013.01); *A61K 31/555* (2013.01); *A61K 31/704* (2013.01); *A61K 49/0442* (2013.01); *A61K 49/0457* (2013.01); *A61K 49/048* (2013.01)

(58) Field of Classification Search
CPC ............ A61K 49/0438; A61K 49/0442; A61K 49/04; A61K 49/048
See application file for complete search history.

(56) References Cited

U.S. PATENT DOCUMENTS

| | | |
|---|---|---|
| 4,406,878 A | 9/1983 | DeBoer |
| 2003/0059371 A1 | 3/2003 | Matson et al. |
| 2004/0101564 A1 | 5/2004 | Rioux et al. |
| 2009/0092675 A1 | 4/2009 | Puri et al. |
| 2011/0052503 A1 | 3/2011 | Almen et al. |

FOREIGN PATENT DOCUMENTS

| | | | |
|---|---|---|---|
| EP | 1810698 A1 | 7/2007 | |
| JP | S5649734 A | 5/1981 | |
| WO | WO-2006119968 A2 * | 11/2006 | ........... A61K 31/704 |
| WO | 2011110589 A1 | 9/2011 | |
| WO | 2013080859 A1 | 6/2013 | |

OTHER PUBLICATIONS

Mawad, Damia, "Synthesis and Characterization of Radiopaque Iodine-Containing Degradable PVA Hydrogels", Biomacromolecules, vol. 9, No. 1, pp. 263-268, 2007.

\* cited by examiner

*Primary Examiner* — James W Rogers
(74) *Attorney, Agent, or Firm* — Seager, Tufte & Wickhem, LLP

(57) ABSTRACT

Radiopaque hydrogels, in particular radiopaque hydrogel microspheres, comprising a polymer having 1,2-dil or 1,3-diol groups acetalized with radiopaque species.

18 Claims, 12 Drawing Sheets

2B

2C

2A

3A

3B (a)

(b)

(c)

(d)

RADIOPAQUE POLYMERS

This is a continuation of Ser. No. 16/733,454, filed Jan. 3, 2020, which is a continuation of U.S. patent application Ser. No. 16/243,672, filed Jan. 9, 2019, now granted as U.S. Pat. No. 10,568,967, which is a continuation of U.S. patent application Ser. No. 14/916,477, filed Mar. 3, 2016, now granted as U.S. Pat. No. 10,350,295, which is a national stage filing International Application No. PCT/GB2014/000352, filed Sep. 5, 2013, the disclosures of which are incorporated herein by reference in their entireties.

This invention relates to imageable, radiopaque polymers and to methods for making radiopaque polymers. The invention is particularly suitable for making radiopaque hydrogels and, in particular, radiopaque hydrogel microspheres, which are imageable during embolization procedures. Such microspheres can be loaded with drugs or other therapeutic agents to provide an imageable drug delivery system.

Radiopacity, or radiodensity, refers to the property of obstructing, or attenuating, the passage of electromagnetic radiation, particularly X-rays. Radiopaque materials thus generally block radiation and are visible in X-ray radiographs or during X-ray imaging and under fluoroscopy. Radiopaque materials consequently find many uses in radiology and medical imaging techniques such as computed tomography (CT) and fluoroscopy.

Embolization of blood vessels is an important medical procedure in the treatment of tumours, fibroids and vascular malformations, in which an embolus is introduced or is formed in a blood vessel to reduce or atop blood flow and induce atrophy of tumours and malformations. There is a range of embolic materials in clinical use that require transcatheter delivery to the site of embolization. This can be achieved with small particles such as poly(vinyl alcohol) (PVA) foam particles (e.g. Ivalon™). However, non-spherical particles suspended in a carrier fluid have a tendency to aggregate, making injection difficult and impractical.

The use of microspheres (also referred to herein as "beads") as injectable biomaterials has become more popular over the last few decades. The tight control over the shape and dimension of injected particles makes them ideally suited for treatments in which the particle size is of critical importance. Microspheres have a controlled shape and size and behave very predictably during the injection procedure. For clinical use, microspheres need to possess a number of characteristics. The microspheres should be biocompatible, safe, stable, display desired functionality inside the patient, and should demonstrate desired and predictable degradation kinetics, i.e they should be non biodegradable or, if biodegradable, they should preferably degrade in a predictable fashion All these parameters are determined by the physico-chemical nature of the synthetic microspheres.

Imaging of embolization procedures is important because it provides the clinician with visual feedback both during and after the procedure. In this way, the clinician can monitor the precise location of the embolic material and ensure that it is administered to, and remains in, the correct position in the vasculature, thus improving procedural outcomes and reducing procedural risk. However, imaging is currently only possible when using inherently radiopaque embolic materials or by mixing non-radiopaque embolic particles with radiopaque materials.

For example, iodinated polyvinyl alcohol (I-PVA) is a radiopaque embolic material in the form of a viscous liquid which precipitates in aqueous conditions such as those encountered in vivo. However, embolization with precipitating liquid can be inconsistent in terms of controlling the precise location at which the embolus is formed and there is always a risk of precipitation occurring in an undesired location outside the target area.

Contrast agents are inherently radiopaque. Common contrast agents include ethiodized oils, such as Ethiodol® (Guerbet Joint Stock Company, France; marketed in the EU under the trade name Lipiodol®). Ethiodol is an iodinated oily X-ray contrast medium composed of an iodinated poppy-seed oil (40% Iodine by weight). Ethiodol® may be used directly as an embolization agent. Due to its viscous nature, the ethiodized oil tends to accumulate in the capillary bed and slow down blood flow. It has thus been described as "microembolic". However, such use is contraindicated by the FDA and, in any event, it fails to provide a reproducible level of embolization. As a result, embolization with ethiodized oil is normally followed by conventional embolization with particles or microspheres to obtain the desired degree of antegrade blood blow.

Other contrast agents include the various ionic and non ionic contrast agents. Soluble contrast media, such as Isovue® (iopamidol, Bracco Diagnostics Inc.) and Omnipaque™ (iohexol, GE Healthcare), are often used in angiography to document the vascular anatomy and monitor blood flow. When soluble contrast medium is mixed with embolic particles, some "parenchymal contrast stain" may be visible for a short duration following the procedure, but this imaging feedback rapidly dissipates.

Contrast agents, such as Ethiodol® and Isovue® are, however, routinely mixed with embolic particles to impart radiopacity to an injectable composition. Although such compositions are useful, the different physical properties of the aqueous suspension of embolic particle and the contrast agent results in different in-vivo localisation. After administration, it is the contrast agent which is visible rather than the embolic particle, and the contrast agent and the embolic particle may not reside at the same location in tissue.

There is a need to combine the predictability and reproducibility benefits of embolic microspheres with the radiopacity of contrast agents.

EP1810698 describes a process for forming stable radiopaque embolic beads (also referred to herein as RO beads or RO microspheres) in which PVA hydrogel embolic beads are loaded with iodinated oils to make them radiopaque. The mechanism by which the oil is held within the bead is unclear. Furthermore, since the oil is a mixture of ethiodised fatty acids, the end product is not closely defined and this approach does not provide control over elution of the contrast agent from the bead nor does it contemplate the impact of contrast agent on the loading and elution of drug.

WO2011/110589 describes synthesis of an iodinated poly (vinyl alcohol) by grafting iodobenzoyl chloride to poly (vinyl alcohol) via ester linkages. Whilst this polymer is demonstrated to be radiopaque, the process results in a water insoluble polymer, which cannot then be formed into microspheres through the water-in-oil polymersation processes normally used to generate hydrogel microspheres with desirable embolization properties. The same publication mentions microspheres but contains no disclosure as to how this is achieved.

Mawad et al (Biomacromolecules 2008, 9, 263-268) describes chemical modification of PVA-based degradable hydrogels in which covalently bound iodine is introduced into the polymer backbone to render the polymer radiopaque. Iodine is introduced by reacting 0.5% of the pendent alcohol groups on PVA with 4-iodobenzoylchloride.

The resulting polymer is biodegradable, embolizes via precipitation and is not formed into microspheres.

There is clearly a need, therefore, for radiopaque embolic materials which combine the embolization efficiency and reproducibility of embolic beads with the radiopacity of contrast agents, such as ethiodized oils, in a single product. The ideal embolic particle is one which is intrinsically radiopaque and which is stable and reproducible, in size and physical properties such that the clinician can perform and image the embolization procedure with more certainty that visible contrast results from the embolic particle. Such radiopaque particles would allow for monitoring of their injection and deposition into the vascular site but would also be very useful for clinical follow-up to monitor the effects of embolization and ensure embolic remains in the desired location and to identify regions at risk for further treatment. The time window in which follow-up imaging can be obtained is increased significantly over existing methods.

Radiopacity (the ability to attenuate X-rays) can be quantified according to the Hounsfield scale. Hounsfield units measure radiopacity on a volume (voxel) basis. A typical voxel in CT is approximately 1 $mm^3$ and so individual microsphere of a diameter of the order of 100 um must have a high radiopacity in order that it, or a collection of them in a vessel (for example) will increase the radiopacity of that voxel and so be visualised. Radiopacity of greater than 100HU and preferably greater than 500HU would be appropriate.

In addition to good radiopacity, the ideal embolic bead would have properties which enable efficient drug loading and elution such that chemoembolization procedures may be monitored with confidence.

The applicants have established that by utilizing relatively straightforward chemistry, it is possible modify polymers to make them radiopaque. A low molecular weight aldehyde comprising one or more covalently attached radiopaque halogens (such as bromine or iodine) is coupled to the polymer by reaction with 1,3 diol groups of the polymer. Reaction with 1,2 glycols is also possible. This forms a cyclic acetal (a dioxane ring in the case of reaction with 1,3,diols) to which is covalently coupled, a halogenated group. The halogenated group has a molecular weight of less than 2000 Daltons and is typically less than 750 Daltons. The minimum is 94 daltons.

The halogenated group may comprise an aromatic or nonaromatic group, such as an aromatic or saturated carbocycle or heterocycle; or an alphatic group and typically has between 1 and 18 carbons, but preferably has a minimum of 2 carbons; preferably between 5 or 6 and 10 carbons; and optionally one, or two hetero atoms (selected from oxygen and nitrogen). Preferably it comprises an aromatic ring comprising one or more covalently attached radiopaque halogens.

The polymer backbone may comprises 1,2 or 1,3 diols, such groups may be present in the polymer backbone, as part of a co-polymer or as side chains or, if the polymer is cross linked, these groups may be present in the crosslinking portion of the polymer. The invention is particularly suited to polymers comprising PVA, such as PVA, PVA co-polymers or to polymers having PVA grafts.

The chemistry results in a polymer having a defined radiopaque group covalently attached to the polymer, in a predictable and controllable fashion. It may be performed on any diol-containing polymer and it is particularly suited to hydrogel polymers and pre-formed microspheres, such that non-radiopaque microspheres may be rendered intrinsically and permanently radiopaque, without adversely affecting the physical properties of the microsphere (i.e. size, spherical shape, high water content, swellability, and compressibility). The radiopaque microspheres have similar, or better, drug loading capacities and elution properties to the non-radiopaque beads from which they are formed. The radiopacity of the microsphere is permanent or sufficiently long-lived to allow for monitoring during clinical follow up.

The ability to post-process pre-formed beads provides a degree of flexibility in terms of manufacturing, in that the same manufacturing process can be used for radiopaque and non-radiopaque beads and size selection or sieving can be made either prior to post-processing so that only a particular size or size range of beads may be made radiopaque, or if necessary, after post processing, so that sizing takes into account any variation in bead size due to the radiopacifying process.

Accordingly, in a first aspect, the present invention provides a polymer comprising 1,2-diol or 1,3-diol groups acetalised with a radiopaque species.

Acetalisation with a radiopaque species results in the radiopaque species being coupled to the polymer through a cyclic acetal group (a dioxane in the case of 1,3 diol polymers). The radiopacity of the polymer is thus derived from having a radiopaque material covalently incorporated into the polymer via cyclic acetal linkages.

As used herein, "radiopaque species" and "radiopaque material" refers to a chemical entity, or a substance modified by such a chemical entity, which is visible in X-ray radiographs and which can be resolved, using routine techniques, such as computed tomography, from the medium that surrounds the radiopaque material or species.

The term microsphere or bead refers to micron sized spherical or near spherical embolic materials. The term particle or microparticle refers to embolic particles that are irregular in shape and are generally derived e.g. from breaking up a larger monolith.

Where the text refers to "halogen" or "halogenated" iodine is preferred, unless otherwise stated.

Reference to the level of radiopacity in HU refers to measurements carried out by X-Ray Micro Computer Tomography, and preferably when measured using a 0.5 mm aluminium filter and a source voltage of 65 kV, preferably in an agarose phantom as described herein (Example 12), preferably using the instrument and conditions described herein (Example 12). Reference to radiopacity in terms of greyscale units also refers to measurements carried out by X-Ray Micro Computer Tomography under these conditions.

Reference to "wet beads" or "fully hydrated beads" means beads fully hydrated in normal saline (0.9% NaCl 1 mM phoshate buffer pH7.2 to 7.4 as packed volume (e.g. as quantified in a measuring cylinder).

In this aspect the polymer can be any one which comprises 1,2-diol or 1,3 diol groups or a mixture thereof. Preferably the polymer comprises a high degree of the diol groups throughout the polymer backbone, such as a polyhydroxypolymer. The polymer is suitably a hydrogel or other cross-linked polymer network. Particularly suitable polymers are those which comprise polyvinyl alcohol (PVA) or copolymers of PVA. PVA based hydrogels are particularly preferred as these are well known in the art and are used extensively in embolization procedures.

The polymer or hydrogel of the invention is radiopaque by virtue of a covalently attached radiopaque material throughout the polymer in the form of a cyclic acetal. Reactions for the formation of cyclic acetals are well known in organic chemistry and, thus, any radiopaque species which is able to form cyclic acetals is envisaged within the scope of the invention. Many materials are known to be radiopaque, such as Iodine, Bismuth, Tantalum, Gadolinium, Gold, Barium and Iron.

Electron dense elements, such as the halogens, are particularly useful. Bromine, chlorine, fluorine and iodine can readily be incorporated into organic molecules which are able to form cyclic acetal linkages and provide a high degree of radiopacity. Consequently, in a particular embodiment the radiopaque polymer comprises a covalently attached halogen, preferably iodine. The radiopaque halogen may be covalently attached to an aromatic or saturated carbocycle or heterocycle to form the radiopaque species which is linked to the polymer through the cyclic acetal. Thus the polymer conveniently comprises a halogenated group (X in the formula below), comprising a covalently bound radiopaque halogen, such as iodine, which is attached to the polymer via a cyclic acetal. In one embodiment, the radiopaque moiety comprises a halogenated aryl group, comprising a covalently bound radiopaque halogen, which is so attached.

Acetalisation with a radiopaque species results in the radiopaque species being coupled to the polymer through a cyclic acetal group as illustrated below. The radiopaque polymer has or comprises a structure according to General Formulas I (in PVA J is —$CH_2$—) or II (which illustrates other polymers with 1,2 or 1,3 diols): Control of the number of such groups acetalised (n) in the polymers controls the amount of iodine present and therefore the radiopacity. The number of diols per gm of material is discussed below.

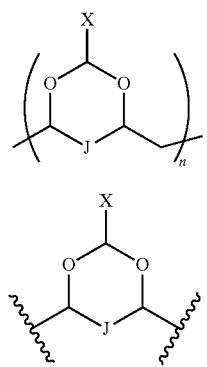

Wherein X is a group substituted by one or more halogens and preferably one or more bromine or iodine moieties and n is at least one J is a group —$CH_2$— or is a bond.

X is preferably a group of the formula

ZQ              III wherein Z is a linking group, or is absent, such that Q is directly bonded to the cyclic acetal;

Z is $C_{1-6}$ alkylene, $C_{2-6}$ alkenylene, $C_{2-6}$ alkynylene, $C_{1-6}$ alkoxylene or $C_{1-6}$ alkoxyalkylene and is optionally substituted by one or more halogens; or is absent;

Q is $C_{1-6}$ alkyl, $C_{2-6}$ alkenyl or $C_{2-6}$ alkynyl group; or is a $C_5$ to $C_{12}$ aryl, or heteroaryl or is a $C_{5-12}$ cycloalkyl; and Q is substituted by one or more halogens.

Preferably Z is $C_{1-6}$ alkylene, $C_{1-6}$ alkoxylene or $C_{1-6}$ alkoxyalkylene; more preferably Z is $C_{1-6}$ alkylene, $C_{1-4}$ alkoxylene or is a group —$(CH_2)_p$—O—$(CH_2)_q$—wherein q is 0, 1 or 2 and p is 1 or 2 or is absent; more preferably Z is a methylene or ethylene group or is a group selected from —$CH_2O$—, —$CH_2OCH_2$— and —$(CH_2)_2O$—, or is absent, such that Q is directly attached to the cyclic acetal;

In particular Z is —$CH_2OCH_2$— or —$CH_2O$— or is absent

Z is preferably not substituted by halogens

In one preferred embodiment, Q is a $C_{1-6}$ alkyl group or a $C_5$ to $C_7$ aryl, $C_5$ to $C_7$ heteroaryl or $C_5$ to $C_7$ cycloalkyl group substituted by 1 or more halogens; more preferably Q is a phenyl, or cyclohexyl group substituted by 1 or more halogens.

In a further embodiment, Q is $C_5$ to $C_7$ aryl, substituted by 1 or more halogens.

Q is preferably substituted by from 1 to 4 halogens, such as 2, 3 or 4 halogens.

Halogens are preferably bromine or iodine, most preferably iodine, thus Q is particularly preferably substituted by 2, 3 or 4 iodines.

Preferably, if Q is $C_{1-6}$ alkyl, $C_{2-6}$ alkenyl or $C_{2-6}$ alkynyl, substituted by one or more halogens, then Z is absent.

Where Q is a heteroaryl group it is preferably pyridyl or pyrimidinyl

Where Q is a cycloalkyl group it is preferably cyclopentane or cyclohexane

Where Q is an aryl group it is preferably phenyl

Q may be, for example, a phenyl group substituted by 2, 3 or 4 bromine or iodines, such as a 2,3,5 or a 2,4,6 triiodophenyl group or a 2,3,4,6 tetraiodophenyl group.

J is preferably —$CH_2$—.

In preferred combinations, Q is a phenyl or cyclohexyl group, and most preferably phenyl, and is substituted by one or more iodines; preferably 1, 2, 3 or 4 iodines and Z is either absent or is a $C_{1-6}$ alkylene, or a group —$(CH_2)_q$—O—$(CH_2)_p$— wherein p is 0, 1 or 2 and q is 1 or 2;

and J is a bond or —$CH_2$—; preferably —$CH_2$—.

Particularly, Q is a phenyl substituted by 3 or 4 iodines and Z is either absent or is a group —$CH_2$—O—$(CH_2)_p$— wherein p is 0 or 1; and J is —$CH_2$—.

Thus preferably, radiopaque iodine is incorporated into the polymer in the form of an iodinated phenyl group. As above, the iodinated phenyl groups are incorporated into the polymer through cyclic acetal linkages.

Groups, such as those described above and in particular halogenated (e.g. iodinated) phenyl groups, are useful because they can be mono, di, tri or even tetra-substituted in order to control the amount of the halogen, such as iodine, that is incorporated into the radiopaque polymer, and hence control the level of radiopacity.

The potential level of halogenation is also influenced by the level of 1,3 or 1,2 diol groups in the polymer starting material. The level can be estimated based on the structure of the polymer and the presence or other wise of any substitutions of the —OH groups, for example by cross linkers or other pendent groups. Polymers having a level of —OH groups of at least 0.1 mmol/g of dried polymer are preferred. Polymers having a level of at least 1 mmol/g are more preferred. An excellent level of radiopacity has been achieved with polymers having greater than 5 mmol/g —OH groups (2.5 mmol/g diols).

It will be understood by the person skilled in the art that the amount of iodine, or other radiopaque halogen, in the polymer may also be controlled by controlling the degree of acetalisation in the polymer. In the present invention, the polymer comprises up to 50% of acetalised diol groups. Preferably at least 10% of the diol groups in the polymer are acetalised and more preferably at least 20% of the diols groups are acetalised. Whether the amount of halogen (e.g. iodine) in the polymer is controlled by increasing the substitution, for example on a phenyl ring, or by controlling the degree of acetalisation of the polymer, the resulting polymer contains at least 10% halogen by dry weight (weight of halogen/total weight). Preferably the polymer contains at least 20% halogen by dry weight and preferably greater than 30%, 40%, 50% or 60% halogen by dry weight. A good level contrast is obtained with polymers having between 30 and 50% halogen by dry weight.

Halogen content may also be expressed as amount of halogen (in mg) per ml of beads. This refers to the amount of halogen per ml of fully hydrated beads in saline as a packed volume (e.g., as quantified in a measuring cylinder). The present invention provides beads with levels of halogen (particularly iodine) of, for example, greater than 15 mg per ml of wet beads. Halogen (particularly iodine) content of greater than 25 or 50 mg preferably greater than 100 mg per ml of beads have provided good results.

The present invention is particularly suited to hydrogels and, in particular, hydrogels in the form of microparticles or microspheres. Microspheres are particularly useful for embolization as sizes of microsphere can be controlled, for example by sieving) and unwanted aggregation of embolic avoided due to the spherical shape. Microspheres can be made by a number of techniques known to those skilled in the art, such as single and double emulsion, suspension polymerization, solvent evaporation, spray drying, and solvent extraction.

Microspheres comprising poly vinylalcohol or vinyl alcohol copolymers are described, for example in Thanoo et al Journal of Applied Biomaterials, Vol. 2, 67-72 (1991); WO0168720, WO03084582; WO06119968 and WO04071495, (which are incorporated herein by reference).

Microspheres can be made in sizes ranging from about 10 μm (microns) to 2000 μm. Smaller sizes may pass through the microvasculature and lodge elsewhere. In most applications it will be desirable to have a small size range of microspheres in order to reduce clumping and provide predictable embolisation. The process used to make the microspheres can be controlled to achieve a particular desired size range of microspheres. Other methods, such as sieving, can be used to even more tightly control the size range of the microspheres.

In a particular embodiment hydrogel or non-hydrogel microspheres according to the invention have a mean diameter size range of from 10 to 2000 μm, more preferably 20 to 1500 μm and even more preferably, 40 to 900 μm. Preparations of microspheres typically provide particles in size ranges to suit the planned treatment, for example 100-300, 300-500, 500-700 or 700-900 microns. Smaller particles tend to pass deeper into the vascular bed and so for certain procedures, particles in the range 40-75, 40-90 and 70-150 microns are particularly useful.

In a particular embodiment, the polymer is a hydrogel microsphere with a net negative charge at physiological pH (i.e. particularly at 7.4).

Radiopacity can be quantified according to the Hounsfield scale, on which distilled water has a value of 0 Hounsfield units (HU), and air has a value of −1000 HU. Conveniently the embolic microsphere will have radiopacity greater than 100HU and even more preferably greater than 500HU. Using the approach described herein, it has been possible to prepare radiopaque microspheres with a radiopacity of greater than 10000HU. Preferred microspheres have a radiopacity greater than 2000, 3000, 4000 or 5000 HU. Radiopacity of these levels allows the microspheres to be differentiated from blood (30-45HU), liver (40-60HU) brain (20-45HU) and soft tissue (100-300HU), for example.

Radiopacity can also be expressed in Grey Scale units, between 0 and 255 after background subtraction, according to American Society for Testing and Materials (ASTM) F-640.

A further aspect of the invention therefore provides, A radiopaque microsphere of the first aspect of the invention, having a radiopacity of at least 500HU.

The hydrogel microspheres of this embodiment may be used in compositions with suitable excipients or diluents, such as water for injection, and used directly to embolise a blood vessel. Thus a further aspect of the invention provides a pharmaceutical composition comprising a hydrogel microsphere as described herein and a pharmaceutically acceptable carrier or diluent.

Consequently pharmaceutical compositions comprising radiopaque hydrogel microspheres which are formed from a polymer comprising 1,2-diol or 1,3-diol groups acetalised with a radiopaque species as described herein, form a further aspect of the invention.

In this aspect, it is preferred that the polymer comprises an iodinated aromatic or non aromatic group such as an aromatic or saturated carbocyclic or heterocyclic group, covalently bound to the polymer through cyclic acetal linkages as described above.

Pharmaceutical compositions comprising the radiopaque microspheres may also comprise additional radiopaque materials, such as, for example contrast agents, (either ionic or non ionic, including oily contrast agents such as ethiodised poppy seed oil (Lipiodol®). Suitable non ionic contrast agents include iopamidol, iodixanol, iohexol, iopromide, iobtiridol, iomeprol, iopentol, iopamiron, ioxilan, iotrolan, iotrol and ioversol.

Ionic contrast agents may also be used, but are not preferred in combination with drug loaded ion exchange microspheres since high ionic concentrations favour disassociation of the ionic drugs from the matrix. Ionic contrast agents include diatrizoate, metrizoate and ioxaglate.

Alternatively, the radiopaque hydrogel microspheres of the invention may be provided in a dried form. Where microspheres or other radiopaque polymer products are provided dry, it is advantageous to incorporate a pharmaceutically acceptable water soluble poly-ol into the polymer before drying. This is particularly advantageous for hydrogels as it protects the hydrogel matrix in the absence of water. Useful poly-ols are freely water soluble sugars (mono or di saccharides), including glucose, sucrose, trehalose, mannitol and sorbitol.

The microspheres may be dried by any process that is recognised in the art, however, drying under vacuum, such as by freeze drying (lyophilisation) is advantageous as it allows the microspheres to be stored dry and under reduced pressure. This approach leads to improved rehydration as discussed in WO07147902 (which is incorporated herein by reference). Typically, the pressure under which the dried microspheres are stored is less than 1 mBar (guage).

Alternatively, or additionally, an effective amount of one or more biologically active agents can be included in the embolic compositions It may be desirable to deliver the active agent from the formed radiopaque hydrogel or from microspheres. Biologically active agents that it may be desirable to deliver include prophylactic, therapeutic, and diagnostic agents including organic and inorganic molecules and cells (collectively referred to herein as an "active agent", "therapeutic agent" or "drug"). A wide variety of active agents can be incorporated into the radiopaque hydrogels and microspheres. Release of the incorporated active agent from the hydrogel is achieved by diffusion of the agent from the hydrogel in contact with aqueous media, such as body fluids, degradation of the hydrogel, and/or degradation of a chemical link coupling the agent to the polymer. In this context, an "effective amount" refers to the amount of active agent required to obtain the desired effect.

Accordingly in a further aspect the invention provides a pharmaceutical composition comprising a radiopaque hydrogel microsphere as described above and a therapeutic agent wherein the therapeutic agent is absorbed into the hydrogel matrix. A further aspect of the invention provides a composition comprising one or more radiopaque hydrogel microspheres as described herein, the microspheres additionally comprising one or more therapeutic agents, such as pharmaceutical actives.

Examples of active agents, or pharmaceutical actives that can be incorporated include, but are not limited to, anti-angiogenic agents, cytotoxics and chemotherapeutic agents, making the microspheres particularly useful for chemoembolization procedures.

In a particularly advantageous embodiment, the radiopaque hydrogel microspheres of the invention have a net charge such that charged drugs may be loaded into the microsphere e.g. by an ion exchange mechanism. As a result, the therapeutic agent is electrostatically held in the hydrogel and elutes from the hydrogel in electrolytic media, such as physiological saline or in-vivo, e.g. in the blood or tissues, to provide a sustained release of drug over several hours, days or even weeks. In this embodiment it is particularly useful if the radiopaque hydrogel microspheres of the invention have a net negative charge over a range of pH, including physiological conditions (7.4) such that positively charged drugs may be controllably and reproducibly loaded into the microsphere, and retained therein electrostatically, for subsequent prolonged elution from the hydrogel in-vivo. Such charges may be derived from ion exchange groups such as carboxyl or sulphonate groups attached to the polymer matrix. It will be understood that drugs without charge at physiological pHs may still be loaded into microspheres of the invention and this may be particularly advantageous when rapid elution or a "burst effect" is desired, for example, immediately after embolization or simply for rapid drug delivery to tissue in cases where embolization is not required or necessary, or where their low solubility under physiological conditions determines their release profile rather than ionic interaction.

Particularly preferred examples of drugs which may be loaded in this way include, but are not limited to, camptothecins (such as irinotecan and topotecan) and anthracyclines (such as doxorubicin, daunorubicin, idarubicin and epirubicin), antiangiogenic agents (such as vascular endothelial growth factor receptor (VEGFR) inhibitors, such as axitinib, bortezomib, bosutinib canertinib, dovitinib, dasatinib, erlotinib gefitinib, imatinib, lapatinib, lestaurtinib, masutinib, mubitinib, pazopanib, pazopanib semaxanib, sorafenib, tandutinib, vandetanib, vatalanib and vismodegib.), microtubule assembly inhibitors (such as vinblastine, vinorelbine and vincristine), Aromatase inhibitors (such as anastrazole), platinum drugs, (such as cisplatin, oxaliplatin, carboplatin and miriplatin), nucleoside analogues (such as 5-FU, cytarabine, fludarabine and gemcitabine) and. Other preferred drugs include paclitaxel, docetaxel, mitomycin, mitoxantrone, bleomycin, pingyangmycin, abiraterone, amifostine, buserelin, degarelix, folinic acid, goserelin, lanreotide, lenalidomide, letrozole, leuprorelin, octreotide, tamoxifen, triptorelin, bendamustine, chlorambucil, dacarbazine, melphalan, procarbazine, temozolomide, rapamycin (and analogues, such as zotarolimus, everolimus, umirolimus and sirolimus) methotrexate, pemetrexed and raltitrexed.

The radiopaque hydrogel microspheres are preferably water-swellable but water-insoluble.

In an embodiment the beads are water-swellable but have some solubility in water. In this embodiment, the extent of swelling may be controlled by the use of aqueous salt solutions or suitable solvents, as may be determined by routine experimentation. This may be particularly applicable to PVA polymers which are non-covalently cross-linked.

In another embodiment the beads are water and solvent-swellable but are also biodegradable. In this embodiment the beads biodegrade in-vivo over a period ranging from 4 weeks to 24 months. Biodegradable polymers comprising PVA are disclosed in, for example, WO2004/071495, WO 2012/101455 and Frauke-Pistel et al. J. Control Release 2001 May 18; 73(1):7-20.

The present inventors have identified, for the first time, that VEGFR inhibitors, such as those listed above, may be loaded into polymeric microspheres such as those discussed herein, and particularly hydrogel microspheres, whether or not they are radiopaque (such as those that have been acetalised with a radiopaque species, as described herein). This can be achieved in the absence of a polyol in the loading medium (as described in WO2012/073188). The compounds may be loaded into polymer beads in acidic solutions (see example 13e) or using a suitable solvent (see example 13c and 13d) after which the drug may be precipitated within the microsphere. This avoids this additional component being present in compositions and microspheres and still avoids precipitation of the drug in the loading medium. If desired, the drug can be made to precipitate within the microsphere, although this is less preferred. The drug is preferably not precipitated within the microsphere. The present invention therefore also provides an embolic microsphere comprising a hydrogel polymer and a VEGFR inhibitor, in the absence of a sugar or polyol, such as glucose, sucrose, dextran, mannitol, sorbitol or trehalose.

The polymer preferably bears a net negative charge at physiological pH (7.4). The VEGFR inhibitor is preferably electrostatically associated with the polymer. Such microspheres preferably comprise PVA or PVA co-polymers, but may be any of the polymers described herein. The polymer may be physically or chemically crosslinked. The invention also encompasses compositions comprising such microspheres as discussed herein for other aspects of the invention. The loaded microspheres can be used to treat the same conditions as the radiopaque microspheres.

As discussed above the radiopaque polymers of the invention may be made by utilizing straightforward chemistry to directly modify pre-formed microspheres to make them intrinsically radiopaque. Accordingly, in a further aspect, the invention provides a method of making a radiopaque polymer comprising reacting a polymer comprising 1,2-diol or 1,3-diol groups with a radiopaque species capable of forming a cyclic acetal with said 1,2-diol or 1,3 diols preferably under acidic conditions.

Particularly the radiopaque species capable of forming the cyclic acetal comprises a covalently bound radiopaque halogen such as iodine as described herein. Particularly the halogen is covalently bound to an aromatic group such as a phenyl group.

The chemistry is particularly suited to polymers with a backbone of units having a 1,2-diol or 1,3-diol structure, such as polyhydroxy polymers. For example, polyvinyl alcohol (PVA) or copolymers of vinyl alcohol containing a 1,3-diol skeleton. The backbone can also contain hydroxyl groups in the form of 1,2-glycols, such as copolymer units of 1,2-dihydroxyethylene. These can be obtained, for example, by alkaline hydrolysis of vinyl acetate-vinylene carbonate copolymers.

Polymers may also comprises 1,2 or 1,3 diols, side chains or, if the polymer is cross linked, these groups may be present in the crosslinking portion of the polymer.

It is also envisaged that polymers that do not comprise 1,2 or 1,3 diol groups, may be modified by the introduction of such groups either as co polymers, into grafts or into crosslinking moieties so that they may be rendered radiopaque in the manner of the invention. Suitable polymers in this instance may be may be for example acrylate, acrylamide and methacrylate polymers (for example polymethacrylic acid polyacrylic acid, polymers of N,N'-methylenebisacrylamide and 2-hydroxyethyl methacrylate and polyacrylamide); poly(ethyleneglycol) and related polymers such as monomethoxypoly(ethyleneglycol), poly(ethyleneglycol)di-acrylamide, poly(ethyleneglycol)di-acrylate, poly(ethyleneglycol) dimethacrylate, poly(ethyleneglycol) methylether methacrylate, propylene glycol, poly(tetramethylene oxide), polymethacrylic acids or polyacrylamides or co polymers of these. Other polymeric diols can be used, such as saccharides.

In a particular embodiment, the polymer is cross-linked, such as cross-linked PVA or copolymers of PVA.

Polymers such as polyvinyl alcohols, that can be derivatized as described herein preferably have molecular weight of at least about 2,000. As an upper limit, the PVA may have a molecular weight of up to 1,000,000. Preferably, the PVA has a molecular weight of up to 300,000, especially up to approximately 130,000, and especially preferably up to approximately 60,000.

Particularly preferred polymers are those comprising PVA which may be physically or chemically cross-linked, including those cross-linked by radiation. These polymers are preferably in hydrogel form. The polymers preferably carry a net negative charge at physiological pH (7.4), especially if they are to be used to load drug. PVA or PVA copolymers, such as PVA 2-acrylamido-2-methylpropanesulphonate (AMPS) polymers, PVA-Bis(acryloyl)L-Cytine (BALC) polymers and PVA acrylate co-polymers are particularly preferred The radiopaque species is acetalised, and covalently attached to the polymer, through diol groups. Preferred radiopaque species are electron dense chemical moieties, such as simple organic molecules or organometallic complexes providing radiopacity greater than +1 HU, and which comprises a reactive moiety that enables formation of a cylic acetal with diol groups on the polymer. Particular reactive moieties include aldehydes, acetals, hemiacetals, thioacetals and dithioacetals In a particular embodiment the radiopaque species comprises bromine or iodine. This is convenient because small organic molecules in which bromine or iodine has been substituted are commercially available or may be prepared using chemistry well known in the art. For example, iodinated or brominated aldehydes are radiopaque and are readily incorporated into diol-containing polymers using the method of the invention. Particularly useful radiopaque species include iodinated or brominated benzyl aldehydes, iodinated phenyl aldehydes and iodinated phenoxyaldehydes.

The reaction of radiopaque aldehydes with diol-containing polymers works surprisingly well with hydrogel polymers, which have been pre-formed, for example into microspheres (although other preformed hydrogel structures such as coatings are contemplated). Thus, in another aspect the invention provides a method of making a radiopaque hydrogel microsphere comprising the steps of:

(a) swelling a pre-formed hydrogel microsphere comprising a polymer with 1,2-diol or 1,3-diol groups in a solvent capable of swelling said microsphere; and (b) mixing or contacting the swollen microspheres with a solution of a radiopaque species capable of forming a cyclic acetal with said 1,2 or 1,3 diols under acidic conditions; and (c) extracting or isolating the microspheres.

The extracted or isolated microspheres may then be used directly, formulated into pharmaceutical compositions as described above or dried for long-term storage.

The reaction is conveniently conducted in polar organic solvent, and more particularly, polar aprotic solvents such as tetrahydrofuran (THF), ethyl acetate, acetone, dimethylformamide (DMF), acetonitrile (MeCN) and dimethyl sulfoxide (DMSO), although suitable solvents will determined by the skilled person through routine experimentation and/or consideration of solvent properties such as boiling point, density etc.

The reaction is rapid and may be conducted at room temperature or at elevated temperature to improve yields and decrease reaction time. In a preferred embodiment the reaction is conducted at a temperature greater than 25° C. and suitably greater than 40° C. but less than 135° C. and preferably less than 80° C. Reaction temperatures between 50 and 75° C. are particularly useful. At elevated temperatures the conversion of hydrogel bead to radiopaque hydrogel bead can be accomplished in as little as 2-3 hours.

As above, the radiopaque species comprises a functional group selected from the group consisting of aldehydes, acetals, hemiacetals, thioacetals and dithioacetals, and comprises iodine or other radiopaque halogen. In this context, the groups such as the acetals and thioacetals may be considered to be protected aldehydes. Iodinated aldehydes, such as iodinated benzyl aldehyde, iodinated phenyl aldehyde or iodinated phenoxyaldehyde, are particularly useful and they are widely available and give good reaction yields.

Thus, preferably the radiopaque species is a compound of the formula IV:

$$X-A \qquad\qquad IV$$

wherein

X is as described above; and

A is a group capable of forming a cyclic acetal with a 1,2 diol or 1,3 diol.

Preferably A is an aldehyde, acetal, hemiacetal, thioacetal or dithioacetal group; Preferably A is —CHO, —CHOR$^1$OR$^2$ —CHOR$^1$OH, —CHSR$^1$OH or —CHSR$^1$SR$^2$ Wherein R$^1$ and R$^2$ are independently selected from C$_{1-4}$ alkyl, preferably methyl or ethyl.

Specific examples of radiopaque species that have been shown to produce radiopaque PVA hydrogel microspheres include 2,3,5-triiodobenzaldehyde, 2,3,4,6-tetraiodobenzyaldehyde and 2-(2,4,6-triiodophenoxy)acetaldehyde In a further aspect the invention provides a radiopaque hydrogel microsphere obtained or obtainable by the reaction of a polymer comprising 1,2-diol or 1,3-diol groups with a halogenated aldehyde, a halogenated acetal a halogenated hemiacetal a halogenated thioacetal or a halogenated dithioacetal The radiopaque and other microspheres and compositions described above may be used in a method of treatment in which the microspheres described herein or composition comprising them are administered into a blood vessel of a patient to embolise said blood vessel. The blood vessel is likely one associated with solid tumour, such as hypervascular hepatic tumours including hepatocellular carcinoma (HCC) and some other hepatic metastases including metastatic colorectal carcinoma (mCRC) and neuroendocrine tumours (NETs). The methods of treatment are imageable and provide the clinician with good visual feedback on the procedure in real-time or near real-time. Such methods are particularly useful where a pharmaceutical active is loaded into the microspheres, and the treatment provides for the delivery of a therapeutically effective amount of the active to a patient in need thereof.

The radiopaque and other microspheres may also be used in procedures in which the microspheres are delivered to the site of action by injection. One approach to this is the delivery of microspheres comprising pharmaceutical actives directly to tumours by injection.

The present invention also provides compositions and microspheres of the invention for use in the methods of treatment described above.

The microspheres described herein are surprisingly efficient in loading and eluting drugs. The microspheres readily load positively charged drugs, such as i.a. doxorubicin, epirubicin, daunorubicin, idarubicin and irinotecan. Experimental studies have shown that the ability of the microsphere to load and elute drug is the same before beads are rendered radiopaque using the chemistry of the invention as it is after reaction. In some cases, drug loading efficiency or capacity is surprisingly improved by more than 50%. In some cases, an increase of 100% in drug loading has been measured. In many cases, the extent of drug elution is unaffected, as compared to the non-radiopaque version of the beads, in some cases with substantially all of the drug eluted from the bead over a sustained period. In many cases the drug elution profile is improved in that the time over which drug is eluted from radiopaque microspheres is increased as compared to equivalent non-radiopaque microspheres. The microspheres of the invention thus, surprisingly provide increased drug loading efficiency and improved i.e. prolonged drug-elution over their non-radiopaque equivalents.

The polymers or microspheres of any of the above aspects and embodiments of the invention may be used in another aspect of the invention in which a method of imaging an embolization procedure is provided. In a further aspect a method of monitoring embolization after the completion of a procedure is provided. Depending on the permanent or rate of biodegradation of the radiopaque polymers of the invention, the post-procedural window in which the embolization may be monitored can be in the range of days, weeks or even months.

The invention will now be described further by way of the following non limiting examples with reference to the figures. These are provided for the purpose of illustration only and other examples falling within the scope of the claims will occur to those skilled in the art in the light of these. All literature references cited herein are incorporated by reference.

FIGURES

FIG. 1 is micrograph of radiopaque hydrogel beads prepared according to the examples. The beads shown are 75-300 μm, sieved after iodination, under different lighting conditions.

FIG. 2 is microCT image of radiopaque beads prepared according to the invention. FIG. 2A is a 3D radiograph of radiopaque beads. FIG. 2B shows a 2D microCT image. The line profile (FIG. 2C) shows: the x-axis (μm) is the length of the line drawn (shown in red across a section of the radiograph; and the y-axis indicates the level of intensity, using grey scale values, ranging from 0 (black) to 255 (white).

FIG. 3 shows light micrographs of sterilized radiopaque beads prepared according to the invention, before and after loading with doxorubicin. FIG. 3A shows the radiopaque beads prior to loading and FIG. 3B shows the drug-loaded beads.

FIG. 4 shows the elution profile of RO and non RO beads loaded with doxarubicin. The beads were 70-150 um in diameter. RO beads were 158 mg I/ml wet beads. Both bead types were loaded with 50 mg doxarubicin per ml wet beads.

Figure 7:
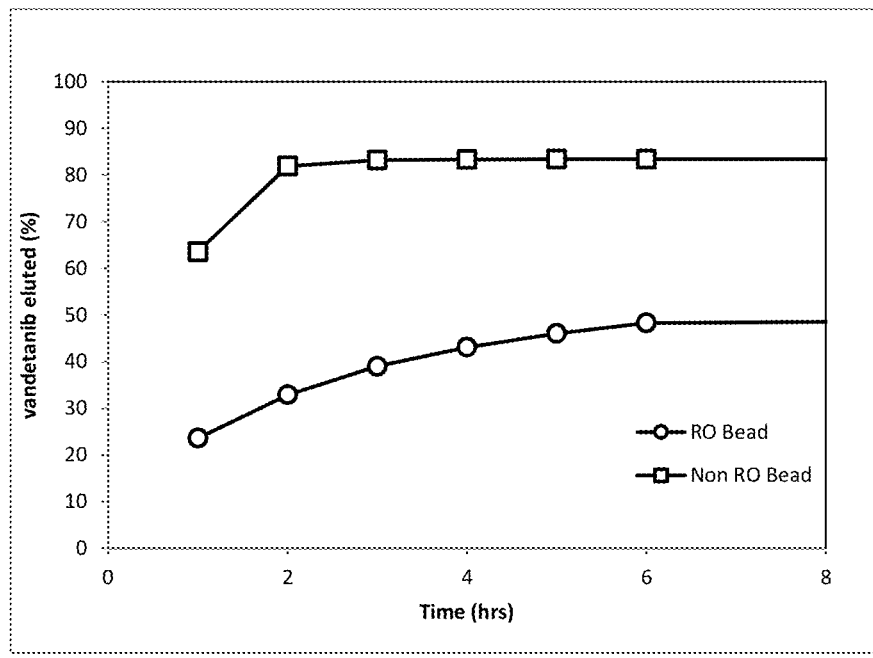

FIG. 7 shows the elution profile of RO and non RO beads loaded with vandetanib. The beads were 70-150 um in diameter. RO beads were 158 mg I/ml wet beads.

Figure 8:
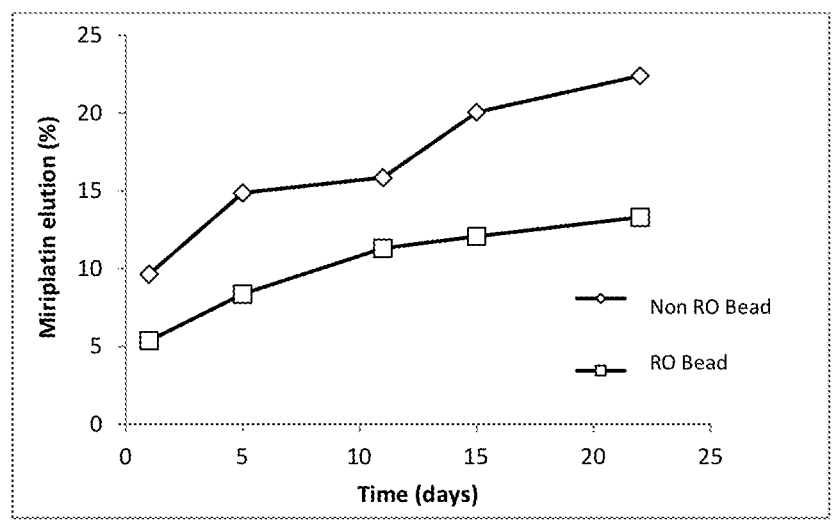

FIG. 8 shows the elution profile of RO and non RO beads loaded with miriplatin. Beads were of size 70-150 um and RO Beads had an iodine content 134 mg I/ml wet beads.

Figure 9:
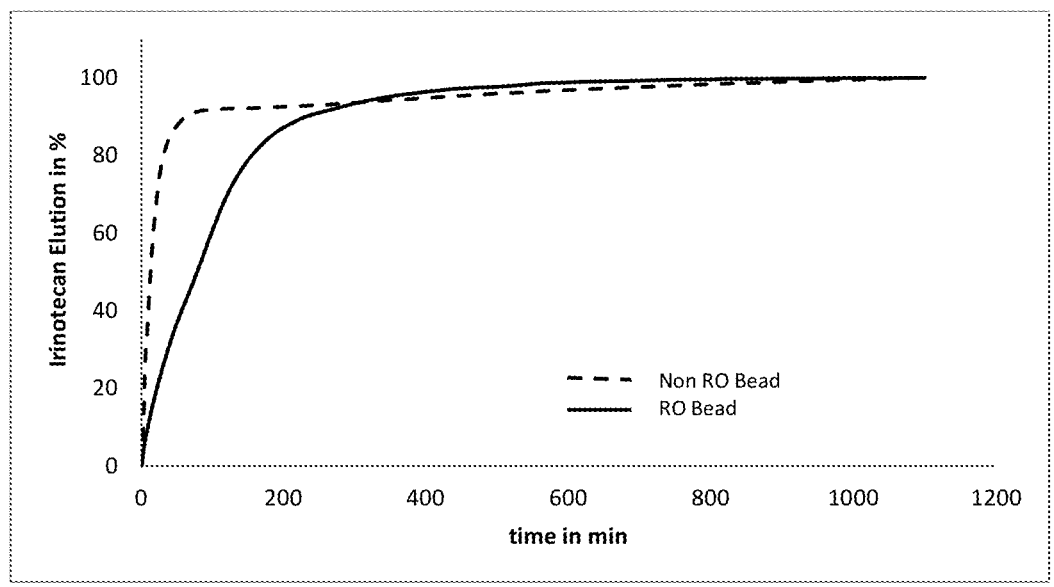

FIG. 9 shows the elution profile of RO and non RO beads loaded with topotecan. RO and Non RO beads had a size of 70-150 um and RO beads had an iodine level of 146 mg I/ml wet beads.

Figure 10:
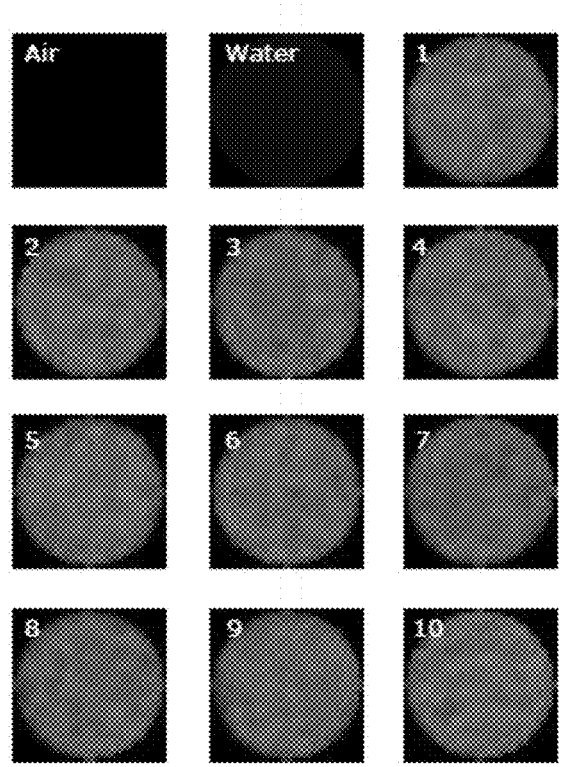

FIG. 10 shows sample cross section micro CT images of 10 RO beads prepared according to the invention alongside water and air blanks.

Figure 11:
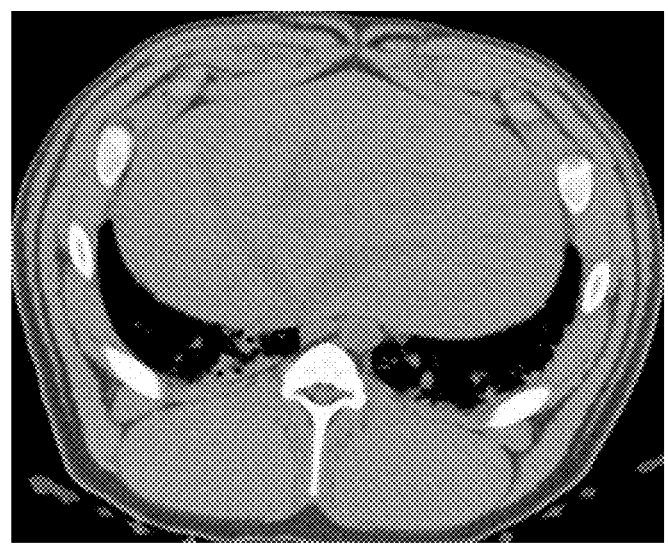
Figure 11:
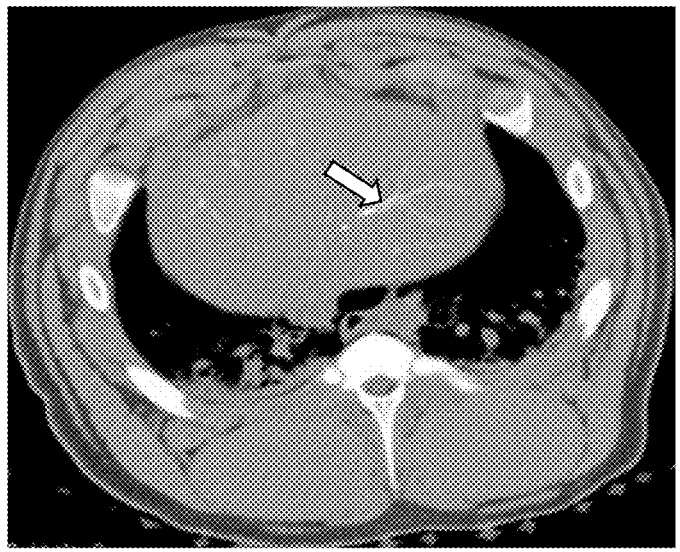
Figure 11:
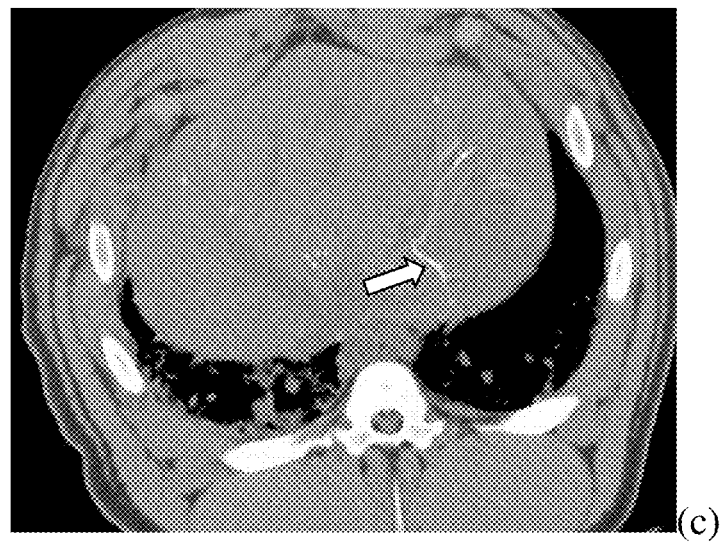
Figure 11:
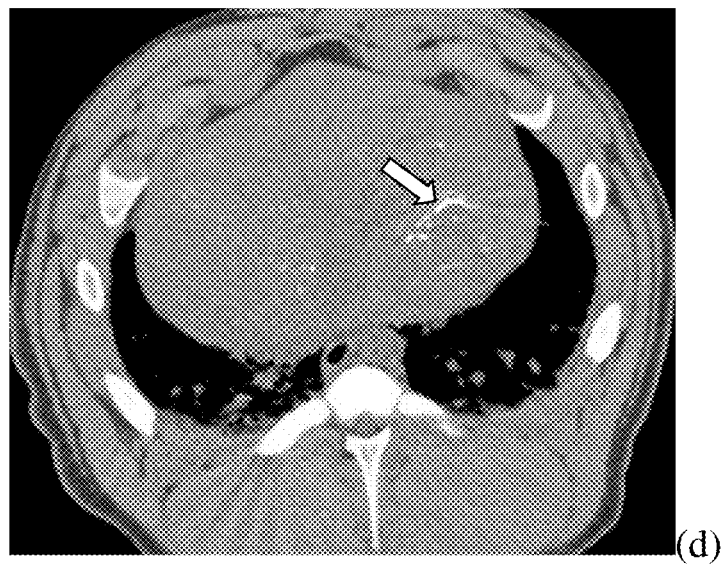

FIG. 11 shows CT scans taken from a single swine following embolisation using the RO beads of the invention.
(a) Pre embolisation; (b) 1 hr post embolisation; (c) 7 days post embolisation; (d) 14 days post embolisation. Arrows indicate RO beads in the vessels.

Throughout these examples the structure of polymer comprising 1,2-diol or 1,3-diol groups is represented by the following structure:

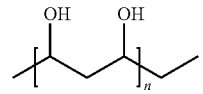

EXAMPLES

Example 1: Preparation of 2,3,5-triiodobenzaldehyde from 2,3,5-triiodobenzyl Alcohol

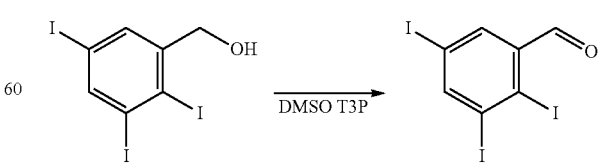

In a 50 ml three-necked round-bottomed flask fitted with a thermometer, a nitrogen bubbler and an air-tight seal, 10.2 g of the alcohol was dissolved in 100 ml of anhydrous DMSO under a nitrogen blanket and stirring conditions. Then, 1.0 molar equivalent of propane phosphonic acid anhydride, (T3P), (50% solution in ethyl acetate) was added drop by drop over 5 minutes at 22° C. to 25° C. The reaction solution was stirred at room temperature and monitored by high performance liquid chromatography (Column: Phenominex Lunar 3 um $C_{18}$: Mobile Gradient: Phase A water 0.05% TFA, Phase B ACN 0.05% TFA, linear gradient A to B over 10 mins: Column temp. 40° C.: flow rate 1 ml per min: UV detection at 240 nm). The conversion finished after 240 minutes. The yellow solution was poured into 100 ml of deionised water while stirring, yielding a white precipitate which was filtered, washed with the mother liquors and 50 ml of deionised water. The cake was slurried in 50 ml of ethyl acetate, filtered and washed with 50 ml of water again, dried sub vacuo at 40° C. for 20 hours to yield 7.7 g of a white solid. The structure and purity were confirmed by NMR analysis and high performance liquid chromatography.

Example 2: Preparation of 2-(2,3,5-triiodophenoxy)acetaldehyde

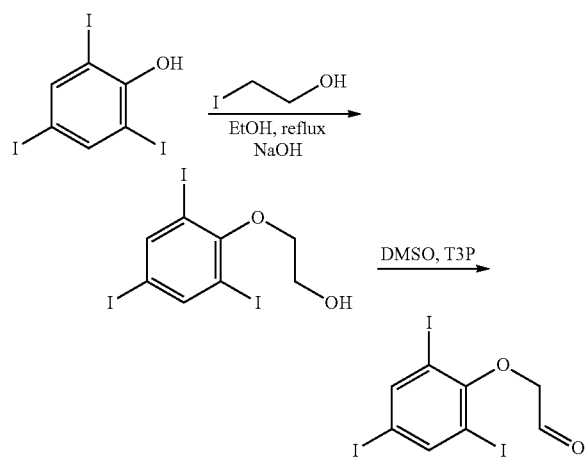

(a) Synthesis of 2-(2,4,6-triiodophenoxy)ethanol from 2,4,6-triiodophenol

In a 500 ml three-necked flat-bottomed flask fitted with a thermometer, a nitrogen bubbler and an overhead stirrer, 10 g of phenol were dissolved in 100 ml of ethanol, under a nitrogen blanket and vigorous stirring conditions at room temperature. 1.25 molar equivalent of sodium hydroxide pellets were added and the slurry was stirred under a nitrogen blanket for 30 minutes until complete dissolution of the pellets. Then, 1.1 molar equivalents of 2-iodoethanol were added, maintaining the temperature at 25° C. and stirring for 15 minutes. The solution was heated to reflux of ethanol. The consumption of the phenol and formation of 2-(2,4,6-triiodophenoxy)ethanol were monitored by HPLC (conditions as per Example 1). After 25 hours, an additional 0.27 molar equivalents of 2-iodoethanol was added and the solution was stirred for a further 2 hours at reflux. After cooling the solution to room temperature, 150 ml of deionised water were added quickly under vigorous stirring conditions. The resulting slurry was filtered under vacuum, washed with the mother liquors, three times 30 ml of deionised water and finally with 5 ml of ethanol. The resulting pink cake was taken up into 100 ml of ethyl acetate and the organic layer extracted with copious amounts of a sodium hydroxide solution (pH14), dried over magnesium sulphate and concentrated on a rotary evaporator to yield 5.9 g of an off-pink solid, which was identified as 2-(2,4,6-triiodophenoxy)ethanol by comparative analysis with a commercial analytical standard from sigma-aldrich.

(b) Oxidation of 2-(2,4,6-triiodophenoxy)ethanol to 2-(2,3,5-triiodophenoxy)acetaldehyde In a 500 ml three-necked flat-bottomed flask fitted with a thermometer, a nitrogen bubbler and an overhead agitator, 5.9 g of the alcohol was dissolved into 150 ml of anhydrous DMSO under a nitrogen blanket. The solution was stirred and heated to 40° C., and 1.6 molar equivalents of T3P (50% w/w solution in EtOAc) were added slowly while maintaining the temperature at 40° C. to 41° C. The consumption of alcohol and production of aldehyde was monitored by high performance liquid chromatography over time (conditions as per Example 1). After 24 hours, 150 ml of water were added slowly to the reaction mixture over 2 hours using a syringe pump. An off-pink solid precipitated out of the solution and was filtered under vacuum to yield a pink cake which was washed with water. The resulting impure flocculate was taken up in ethyl acetate and hexane, then concentrated under vacuum at 40° C. to yield an oil identified as 2-(2,3,5-triiodophenoxy)acetaldehyde by $^1$H NMR analysis.

Example 3: Preparation of 1-(2,2-dimethoxyethoxymethyl)-2,3,5-triiodo-benzene from 2,3,5-triiodobenzyl alcohol and 2-bromo-1,1-dimethoxyethane (Example of a Radiopaque Acetal/Protected Aldehyde)

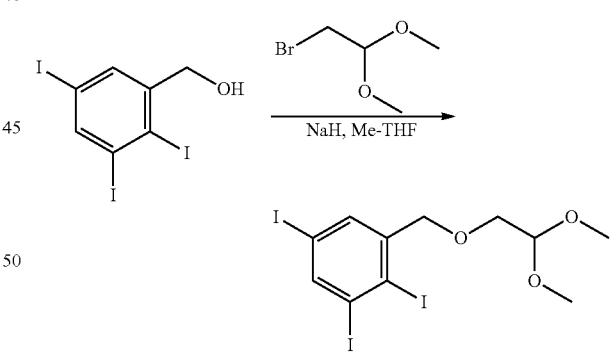

In a 50 ml three-necked flat-bottomed flask fitted with an overhead agitator, a thermometer, a nitrogen bubbler and a gas tight septum, 5.07 g of the alcohol were dissolved in 55 ml of anhydrous 2-methyltetrahydrofuran under a nitrogen blanket and stirring conditions. Then, 2.11 g of the acetal followed by 0.540 g of sodium hydride (60% dispersion in mineral oil) were added. The slurry was heated to reflux under a nitrogen blanket for 1010 minutes and monitored by high performance liquid chromatography (conditions as per Example 1). The reaction mixture was taken up into 50 ml of dichloromethane and washed four times with 25 ml of water. The organic layer was concentrated sub vacuo to yield a brown oil, which was identified as 1-(2,2-dimethoxy-ethoxymethyl)-2,3,5-triiodo-benzene by ¹H NMR.

Example 4: Preparation of Cross-Linked Hydrogel Microspheres

Cross-linked hydrogel microspheres were prepared according to Example 1 of WO 2004/071495. The process was terminated after the step in which the product was vacuum dried to remove residual solvents. Both High AMPS and low AMPS forms of the polymer were prepared and beads were sieved to provide appropriate size ranges. Beads were either stored dry or in physiological saline and autoclaved. Both High AMPS and low AMPS forms of the polymer can used with good radiopacity results.

Example 5: General Preparation of Radiopaque Microspheres from 2,3,5-Triiodobenzaldehyde and Preformed Cross-Linked PVA Hydrogel Microspheres

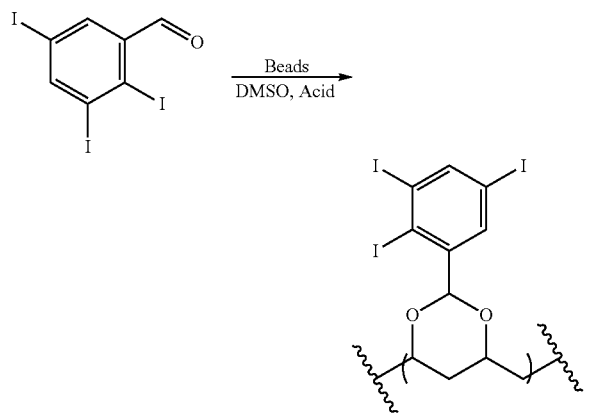

In a 50 ml three-necked round-bottomed flask fitted with an overhead agitator, a thermometer and a nitrogen bubbler, 1.0 g of dry PVA-based beads (see Example 4—High AMPS version) were swollen in an appropriate solvent (e.g. DMSO) under a nitrogen blanket and stirring conditions. Then, 0.20 to 1.5 molar equivalents of aldehyde (prepared according to Example 1) were added to the slurry, immediately followed by 1.0 to 10 molar equivalents of acid (e.g. sulphuric acid, hydrochloric acid, methanesulfonic acid or trifluoroacetic acid—methanesulfonic acid is typically used). The theoretical level of available —OH groups was estimated based on the characteristics of the PVA used and the degree of cross linking (typical values for high AMPS beads=0.0125 mol/gm dry beads). The reaction slurry was stirred at 50° C. to 130° C. for between 12 hours and 48 hours, while the consumption of aldehyde was monitored by high performance liquid chromatography (HPLC). When required, a desiccant such as magnesium sulphate or sodium sulphate was added to drive the reaction further. In this way batches of radiopaque microspheres having differing levels of iodine incorporation could be obtained. When enough aldehyde had reacted on the 1,3-diol of the PVA-based hydrogel to render it sufficiently radiopaque (see below), the reaction slurry was cooled to room temperature and filtered. The cake of beads was washed with copious amount of DMSO and water, until free from any unreacted aldehyde, as determined by high performance liquid chromatography.

Example 6: Preparation of Radiopaque Microspheres from 2,3,5-Triiodobenzaldehyde and a Cross-Linked PVA Hydrogel Microsphere 5.0 g of dry PVA-based beads (see Example 4—High AMPS version 105—150 um) and 0.26 equivalents of aldehyde (7.27 g) (prepared according to Example 1) placed in a 500 ml vessel purged with nitrogen. 175 ml anhydrous DMSO were added under a nitrogen blanket and stirred to keep the beads in suspension. The suspension was warmed to 50 C and 11 ml of methane sulphonic acid was added slowly. The reaction slurry was stirred at 50° C. for between 27 hours, while the consumption of aldehyde was monitored by HPLC. The reaction slurry was then washed with copious amount of DMSO/1% NaCl followed by saline. The resultant beads had an iodine concentration of 141 mg I/ml wet beads and had a radiopacity of 4908HU.

Example 7: Preparation of Radiopaque PVA Hydrogel Beads with 2-(2,4,6-Triiodophenoxy)Acetaldehyde

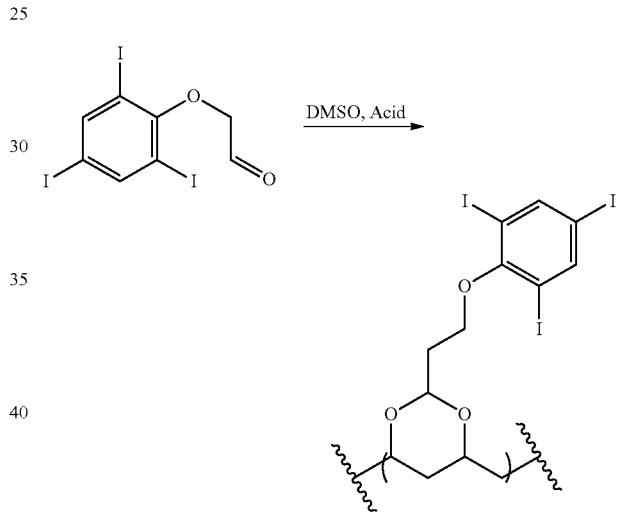

2-(2,4,6-triiodophenoxy)acetaldehyde was prepared according to Example 2 and reacted with PVA-based hydrogel beads (see Example 4 high AMPS version) following the same method as Example 5 but with the temperature of the reaction maintained between 20° C. and 50° C. The reaction time was also reduced to less than one hour. Iodine content was determined to be 18 mg I/ml wet beads.

Example 8: Preparation of Radiopaque PVA Hydrogel Microspheres with 1-(2,2-Dimethoxyethoxymethyl)-2,3,5-Triiodo-Benzene

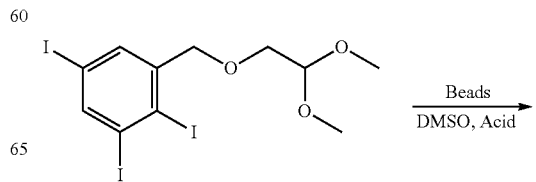

-continued

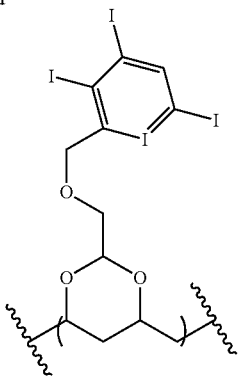

In a 50 ml three-necked flat-bottomed flask fitted with an overhead agitator, a thermometer and a nitrogen bubbler, 1.0 g of dry PVA-based beads (see Example 4 high AMPS version) were swollen in an appropriate solvent (e.g. DMSO) under a nitrogen blanket and stirring conditions. Then, 0.5 molar equivalents of aldehyde (1-(2,2-dimethoxy-ethoxymethyl)-2,3,5-triiodo-benzene, prepared according to Example 3) were added to the slurry, immediately followed by 163 μl of methanesulfonic acid. The reaction slurry was stirred at 40° C. for 80 minutes, and then heated to 80° C. for 200 minutes, while the consumption of aldehyde was monitored by high performance liquid chromatography. As enough aldehyde had reacted on the 1,3-diol of the PVA-based hydrogel to render it sufficiently radiopaque after this time, the reaction slurry was cooled to room temperature and filtered. The cake of beads was washed with copious amounts of DMSO and water, until free from any unreacted acetal and aldehyde, as determined by high performance liquid chromatography. Iodine content of the beads was determined to be 31 mg/ml wet beads.

Example 9: Preparation of Radiopaque PVA Hydrogel Microspheres from 2,3,4,6 Tetraiodobenzaldehyde 2,3,4,6-tetraiodobenzyl alcohol (ACES Pharma; USA) was converted to 2,3,4,6 tetraiodobenzaldehyde using T3P and DMSO as described in Example 1. 0.6 molar equivalents of 2,3,4,6 tetraiodobenzaldehyde (8.8 g) was then added to 2.05 g of PVA hydrogel microspheres (see Example 4—size 150-250 μm high AMPS version) with DMSO under a nitrogen blanket. The reaction mix was heated to 50° C. and stirred for several hours. The reaction was monitored with HPLC and when complete, the beads were filtered and washed with DMSO, water and then 0.9% saline. The radiopaque beads were then stored in a solution of 0.9% saline for analysis. Iodine content was determined to be 30 mg/ml wet beads.

Example 10: Preparation of Radiopaque Microspheres of a PVA—Sodium Acrylate Co-Polymer Using 2,3,5-Triiodobenzaldehyde 0.1 g of dried PVA-sodium acrylate co-polymer microspheres (Hepasphere® (Merit Medical Systems Inc.) of size range 150-200 μm was mixed with 0.1314 g of 2,3,5-triiodobenzaldyde dissolved in 3.5 ml of anhydrous DMSO. The reaction was heated to 50° C. with stirring under nitrogen. After 10 mins. stirring, 0.22 ml of methanesulfonic acid was added and the reaction was allowed to proceed at 50° C. for 24 hr. The beads were then washed with 20 ml of DMSO 1% NaCl, 5 times at 50° C., each wash lasting 10 mins. The beads were then washed with 20 ml of 0.9% saline for 10 mins with shaking.

Elemental analysis showed mean iodine levels (n=2) of 25.21% w/w dry beads.

Example 11: Characterization of Radiopaque Beads

Figure 1:
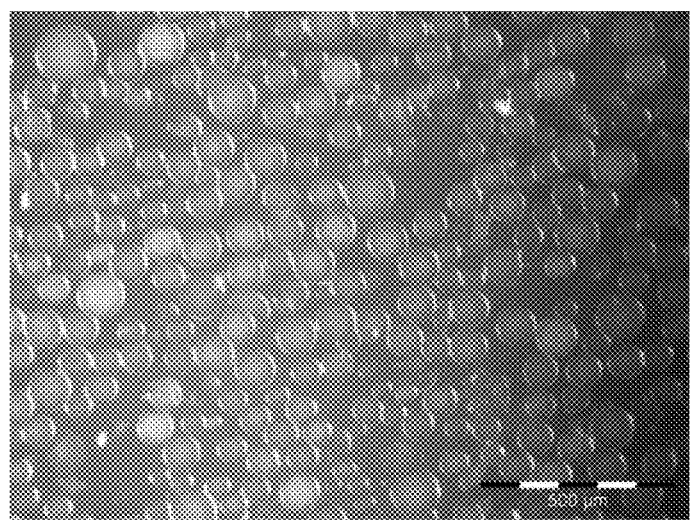
Figure 1:
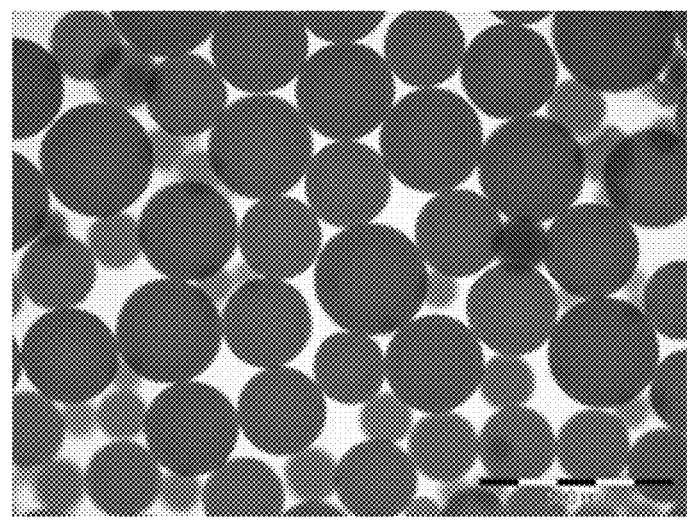

A light micrograph of the beads, typical of those produced by Examples (5 and 6) is shown in FIG. 1.

The dry weight of beads was measured by removing the packing saline and wicking away remaining saline with a tissue. The beads were then vacuum dried under 50° C. overnight to remove water, and the dry bead weight and solid content (w/w %) of polymer were obtained from this.

The iodine content (w/w %) in dry, beads were measured by elemental analysis according to the Schaniger Flask method. For iodine content in wet beads, the calculation is:

Bead solid content (%)×iodine content in dry beads (%)

The solid content of radiopaque hydrogel beads, prepared according to Example 5 in a 0.9% saline was measured to be between 5% and 16%, w/w, while the weight/weight dry iodine content was measured to be between 5% and 56%, depending on the chemistry and the reaction conditions used.

An alternative way to express the iodine content is mg I/mL wet beads (wet packed bead volume), which is the same as the unit used for contrast media. Using protocols according to Example 5, iodine content in the range 26 mg I/ml beads to 214 mg I/ml beads was achieved.

Using similar protocols, but microspheres based on a low AMPS polymer (Example 4), higher iodine contents (up to 250 mg I/ml beads) could be achieved.

Example 12—MicroCT Analysis of Radiopaque Beads

Micro-CT was used to evaluate the radiopacity of samples of radiopaque embolic beads prepared according to Example 5 above. The samples were prepared in Nunc cryotube vials (Sigma-Aldrich product code V7634, 48 mm×12.5 mm). The beads were suspended in 0.5% agarose gel (prepared with Sigma-Aldrich product code A9539). The resulting suspension is generally referred to as a "Bead Phantom". To prepare these bead phantoms, a solution of agarose (1%) is first raised to a temperature of approximately 50° C. A known concentration of the beads is then added, and the two gently mixed together until the solution starts to solidify or gel.

As the solution cools it gels and the beads remain evenly dispersed and suspended within the agarose gel.

Bead phantoms were tested for radiopacity using micro-Computer Tomography (μCT) using a Bruker Skyscan 1172 μCT scanner at the RSSL Laboratories, Reading, Berkshire, UK, fitted with a tungsten anode. Each phantom was analysed using the same instrument configuration with a tungsten anode operating at a voltage of 64 kv and a current of 155 μA. An aluminium filter (500 μm) was used.

Acquisition parameters:
Software: SkyScan1172 Version 1.5 (build 14)
NRecon version 1.6.9.6
CT Analyser version 1.13.1.1

Source Type: 10 Mp Hamamatsu 100/250
Camera Resolution (pixel): 4000×2096
Camera Binning: 1×1
Source Voltage kV: 65
Source Current uA: 153
Image Pixel Size (um): 3.96
Filter: Al 0.5 mm
Rotation Step (deg): 0.280
Output Format: 8 bit BMP
Dynamic Range: 0.000-0.140
Smoothing: 0
Beam Hardening: 0
Post Alignment: corrected
Ring Artefacts: 16

A small amount of purified MilliQ water was carefully decanted into each sample tube. Each sample was then analysed by X-Ray micro-computer tomography using a single scan, to include the water reference and the beads. The samples were then reconstructed using NRecon and calibrated against a volume of interest (VOI) of the purified water reference. A region of interest (ROI) of air and water was analysed after calibration to verify the Hounsfield calibration.

Figure 2:
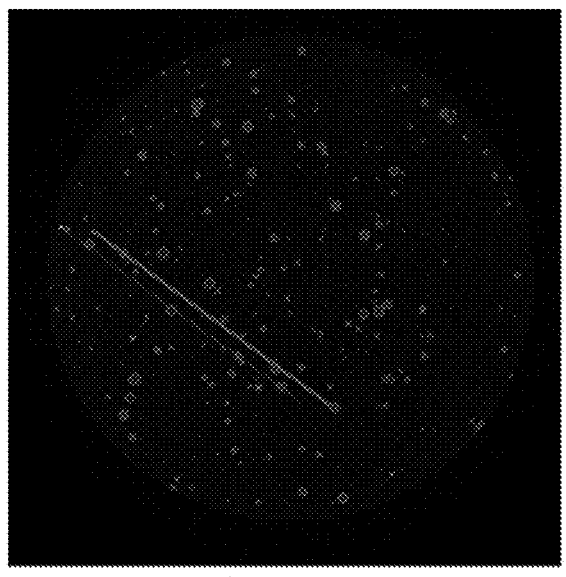
Figure 2:
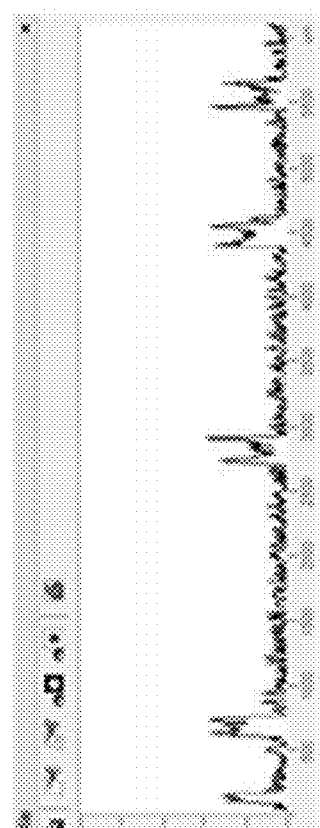
Figure 2:
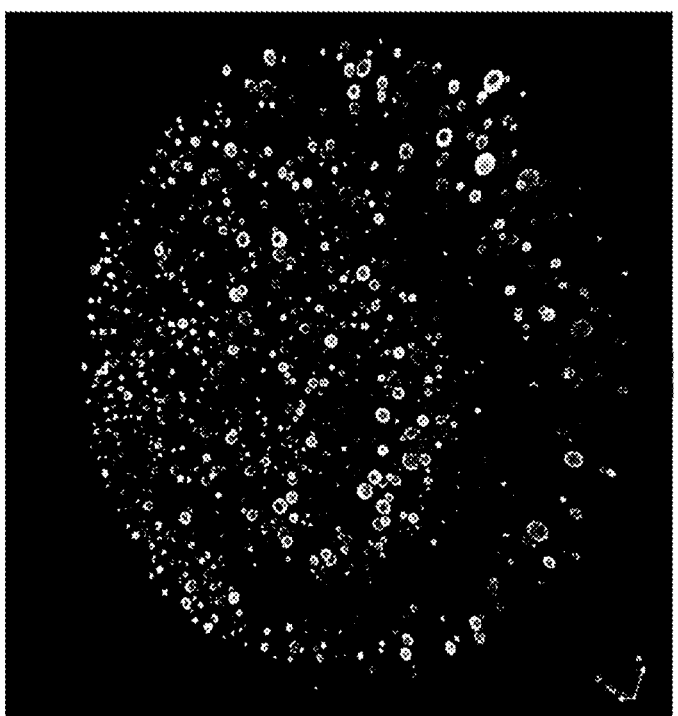

Radiopacity was reported in both greyscale units and Hounsfield units from line scan projections across the bead. Values used for dynamic range for all samples in NRecon (thresholding): −0.005, 0.13 (minimum and maximum attenuation coefficient). A typical image and line scan is shown in FIG. 2.

Table 1 gives the radiopacity of microspheres prepared according to Example 4 under varying conditions of time and equivalents of aldehyde, in both greyscale and Hounsfield units. Radiopacity data are the mean of ten line scans of beads of approximately 150 microns.

TABLE 1

| Iodine (mg I/ml) | Grey scale | HU | Mean bead size (um) |
|---|---|---|---|
| 158 | 79 | 5639 | 158 |
| 147 | 69 | 4626 | 146 |
| 141 | 74 | 4799 | 131 |
| 130 | 56 | 3600 | 153 |

FIG. 10 shows a sample of cross section images of 10 beads with an average size of 153 um, and average radiopacity of 4908HU.

Example 13 Drug Loading of Radiopaque Beads

Example 13 (a) Doxorubicin 1 mL of RO bead slurry prepared according to Example 5 (size 100-300 um, iodine 47 mg I/ml wet beads) was measured by using a measuring cylinder, and the liquid removed. 4 mL of doxorubicin solution (25 mg/mL) was mixed with the radiopaque beads with constant shaking at ambient temperature. After 20 hr loading, the depleted solution was removed, and the drug-loaded beads were rinsed with deionised water (10 mL) 4-5 times. By measuring the doxorubicin concentration of combined depleted loading solution and rinsing solutions at 483 nm on a Varian UV spectrophotometer, the doxorubicin loaded was calculated as 80 mg/mL beads. The doxorubicin hydrochloride drug loading capacity of the radiopaque beads was determined to be a non-linear function of the iodine content in the beads.

In a separate experiment 1.5 ml of RO beads of 70-150 um having an iodine content of 158 mg/ml wet beads were loaded as above using 3 ml of doxorubicin solution (25 mg/ml). Control, non RO beads of the same size, were also loaded in the same manner. The RO beads loaded 50 mgs/ml of doxorubicin whilst the control beads loaded 37.5 mgs/ml.

In a separate experiment, loading of RO beads (size 70-150 um; iodine content 150 mg I/ml), was essentially complete after 3 hrs.

Figure 3:
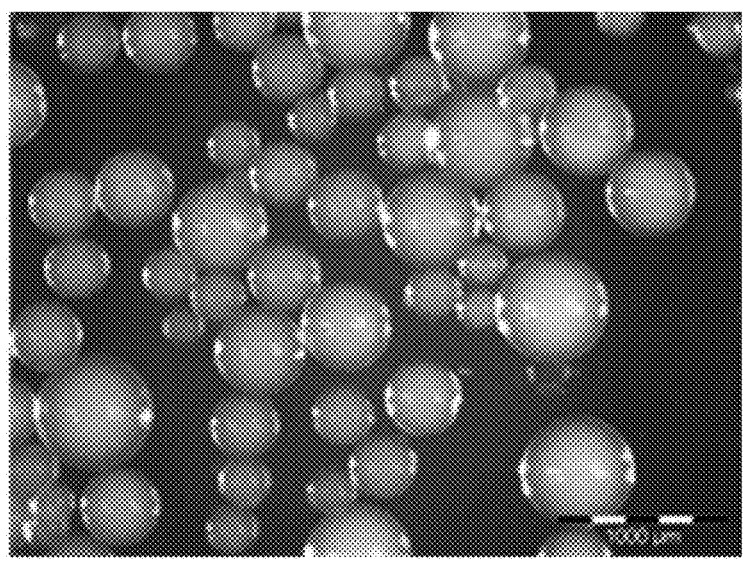
Figure 3:
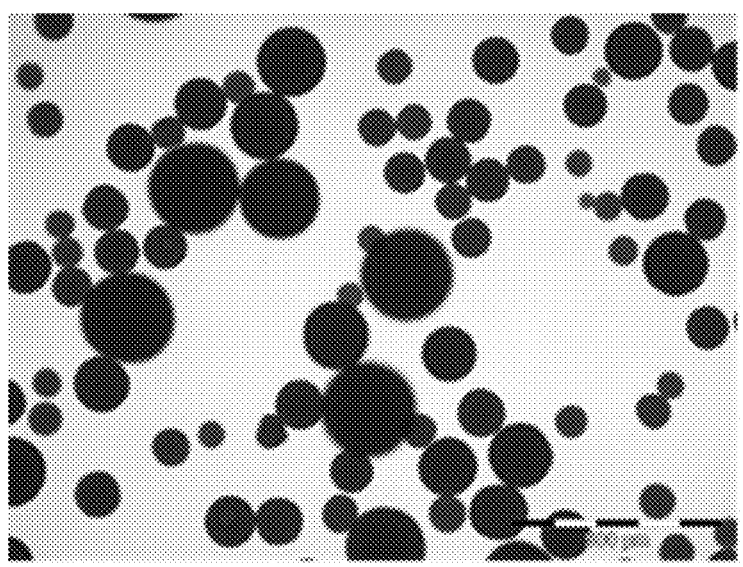

Radiopaque beads prepared according to Example 5 above were loaded with 37.5 mg/ml of doxorubicin solution as per the above method. FIG. 3A shows the radiopaque beads prior to loading and FIG. 3B shows the drug-loaded beads. Prior to drug loading the beads were observed as spherical microspheres with a pale to dark brown tinge. When the doxorubicin was loaded into the beads they turned a strong red colour. In this example, the beads were autoclaved to demonstrate to stability of the beads during sterilization. Bead integrity was preserved during autoclaving; the mean bead size during autoclaving reduced from 177 μm to 130 μm. Further shifts in the bead size distribution were observed when beads were loaded with doxorubicin, which is consistent with drug-loading observed with non-radiopaque beads. In a further example, the mean bead size reduced on drug loading at 51 mg/ml, from 130 μm to 102 μm. The resulting beads remain within the range that is clinically useful, even after modification, sterilization, and drug-loading.

Example 13(b) Epirubicin

Epirubicin was loaded into RO beads (made according to Example 5) and non RO beads (size, 70-150 um) in the same manner as for doxorubicin. 1 ml of beads was loaded using a 1.5 ml loading solution (25 mg/ml epirubicin). The final loading in the radiopaque beads was 37.49 mg (99.97% loading efficiency) and for the non RO beads 36.43 (97.43% loading efficiency) after 90 mins.

Example 13(c) Sunitinib

Sunitinib DMSO solution was prepared by dissolving 400 mg of sunitinib powder in anhydrous DMSO in a 10 mL volumetric flask. 1 ml of RO bead slurry (70-150 um, 134.4 mg I/ml wet beads prepared according to Example 5). was prewashed with 10 ml of DMSO three times to remove water residue. 2.5 mL of the sunitinib-DMSO solution (40 mg/mL) was mixed with the RO bead slurry and allowed to mix for 1-2 hr. Subsequently, after removing the loading solution, 10 mL of saline was added to the bead slurry to allow sunitinib to precipitate inside the beads. The wash solution and drug particles were filtered through a cell strainer, and the washing was repeated three to four times. Non RO beads (100-300 um, prepared according to Example 4) were treated in the same manner.

Example 13(d) Sorafinib 1 ml of RO PVA microspheres (size 70 to 150 um, iodine content 134 mg iodine/ml beads, prepared according to Example 5) or non RO PVA microspheres (DC Bead™ 100-300, Biocompatibles; UK) were prewashed with 10 ml of DMSO three times to remove water residue. Sorafenib/DMSO solution (39.8 mg/mL in anhydrous DMSO) was mixed with 1 mL of bead slurry for 1 hr, (2.5 mL for the radiopaque bead and 2 mL for the non radiopaque bead). After removing the loading solution, 20 mL of saline was added to the bead slurry. The bead suspension was filtered through a cell strainer, and the wash was repeated three or four times. The final loading level was determined by DMSO extraction of small fraction of hydrated beads and determination of drug concentration by HPLC (Column: Kinetex 2.6u XB-C18 100 A 75×4.60 mm; mobile phase water:acetonitrile:methanol:trifluoroacetic acid 290:340:370:2 (v/v); detection 254 nm; column temperature 40° C.; flow rate: 1 mL/min). 49.9 mg of sorafinib was loaded into 1 ml RO beads and 34.7 mg was loaded into 1 ml of non-RO (DC Bead™) beads.

Example 13(e) Vandetinib

A solution of 20 mg/ml vandetanib was prepared by dissolving 500 mg of vandetanib in 14 ml of 0.1M HCl in a 25 ml amber volumetric flask with sonication, and making up to 25 ml with deionised water. Vandetanib was then loaded into both RO PVA hydrogel microspheres (prepared according to Example 5: Size 70 to 150 um; Iodine content 147 mg/ml beads) and non-RO microspheres (DC Bead 100-300; Biocompatibles UK Ltd) according to the following protocol:

One millilitre of microspheres including packing solution was aliquoted by measuring cylinder and transferred into a 10 mL vial. The packing solution was then removed using a pipette. Three millilitres of the 20 mg/ml drug solution was then added to the non RO bead or 1.5 mL of the solution to RO beads. In the radiopaque bead loading experiment the pH of the solution was between 4.6 and 4.8; in the DC bead loading experiment the pH was at approximately 4.2. This maintains the drug in the charged form. After 2 hr. loading, the residual solution was removed, and the beads were washed with 5 mL of deionised water 3 times. The drug was not precipitated inside the beads. The depleted loading and washing solutions were combined and analysed by Cis reverse phase HPLC with detection at 254 nm to determine the loading yield. For sterilisation if, needed, the loaded beads, in 1 ml of deionised water, were either autoclaved at 121° C. for 30 min, or lyophilised for 24 hr and then gamma sterilised at 25 kGy.

Radiopaque beads loaded vandetanib to a level of 29.98 mg/ml of wet beads.

Non radiopaque beads loaded vandetanib to a level of 26.4 mg/ml.

Example 13(f) Miriplatin

Hydrated RO microspheres (size 70-150 um, iodine content 134 mg iodine/ml beads, prepared according to Example 5) and non RO PVA microspheres (DC Bead 100-300, Biocompatibles; UK), 1 mL each vial, were washed with 5 mL of 1-methyl-2-pyrrolidinone four times. The solvent was then removed. 0.147 g of miriplatin was mixed with 25 mL of 1-methyl-2-pyrrolidinone, and the suspension was heated to 75° C. in a water bath to dissolve miriplatin. 2 mL of the drug solution was added into the washed beads and the mixture placed in a 75° C. water bath for 1 hr. The bead suspensions were filtered through a cell strainer to remove the loading solution, followed by washing with about 100 mL of saline.

A known volume of beads was washed with deionised water and freeze dried. Total platinum was determined by elemental analysis using ICP-OES (Inductively Coupled Plasma—Optical Emission Spectroscopy) and converted to miriplatin level.

The experiment was repeated loading lyphilised beads in the same manner. Table 2 shows the results of loading miriplatin into wet and lyophilised RO beads.

TABLE 2

Miriplatin loading data.

| Bead sample | Miriplatin content (%) | Miriplatin in wet beads (µg) |
|---|---|---|
| Non RO bead (wet loaded) | 0.39 | 2058 |
| RO Bead (wet loaded) | 0.31 | 2645 |
| RO bead (dry loaded) | 0.12 | 1160 |

Example 13(g) Irinotecan

A 2 mL bead sample of Non RO beads (100-300 um—made according to Example 4 high AMPS version) and RO Bead (100-300 um, 163 mg I/mL made according to Example 5) were mixed with 10 ml irinotecan solution in water (10 mg/mL). Loading was measured by determining the irinotecan level in depleted loading solution by UV spectroscopy, at 384 nm. Both non RO and RO beads loaded approximately 100% of the drug within 90 min.

Example 13(h) Topotecan

A 1 mL bead sample of Non RO beads (70-150 um—made according to Example 4 high AMPS version) and RO Bead (70-150 um, 146 mg I/mL made according to Example 5) were mixed with topotecan solution in water (15.08 mg/mL) to load dose of 40 mg (2.5 ml) or 80 mg (5 ml) under agitation. After about 1.5 hr, the loading of topotecan was measured by determining the topotecan level in depleted loading solution as described above, by UV spectroscopy, at 384 nm. Table 3 shows maximum of 80 mg topotecan was loaded in RO bead sample. Both non RO and RO beads loaded >98% of 40 mg topotecan.

TABLE 3

Topotecan loading in RO and non RO beads

| | Time (hrs) | Drug loaded (mg) | % Drug Loaded |
|---|---|---|---|
| RO bead, 1 mL | 1.5 | 40 | 100 |
| RO bead, 1 mL | 1.5 | 80 | 100 |
| Non RO bead, 1 mL | 1.5 | 39 | 98 |

Example 14 Drug Elution from Radiopaque Beads

Example 14(a) Doxorubicin

Figure 4:
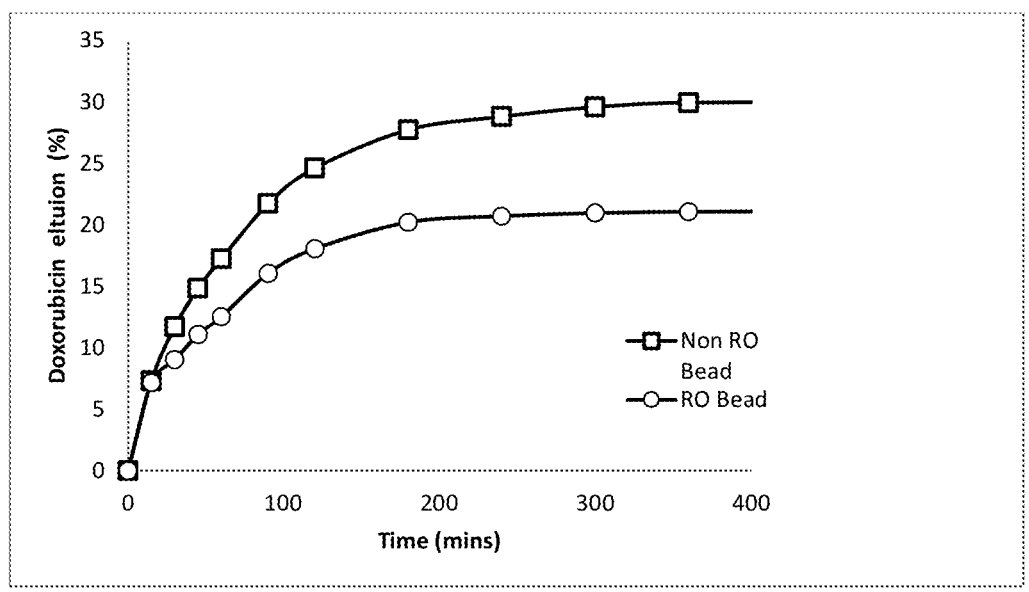
Figure 5:
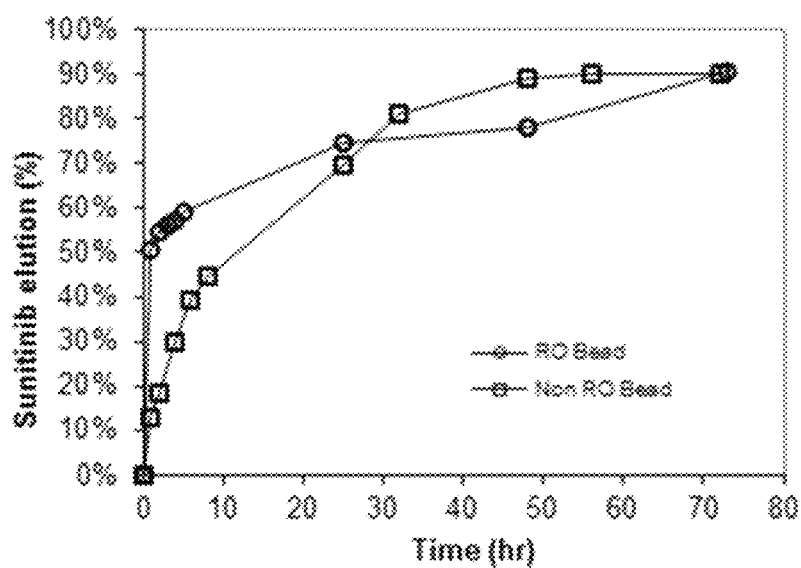
FIG. 5 shows the elution profile of RO beads loaded with sunitinib.

Doxorubicin-loaded beads prepared in the according to Example 13(a) (70-150 um, 158 mg I/ml, 50 mg/ml doxorubicin) were added to 1000 ml of PBS, in a brown jar at room temperature. The bead suspension was stirred with a magnetic stirrer at low speed. At sampling time points, 1 mL of elution media were removed through a 5 um filter needle and analysed by UV at 483 nm against a standard. The elution profiles were shown in FIG. 4.

Example 14(b) Sunitinib

Sunitinib-loaded beads prepared according to Example 13(c) were added to 400 ml of PBS, 0.5 g/L Tween 80 in a brown jar at 37° C. in a water bath. The bead suspension was stirred with a magnetic stirrer at low speed. At sampling time points of 1, 2, 3 and 4 hours, 10 mL of elution media were removed through a 5 um filter needle for HPLC analysis (conditions as per Example 13(c)) and 10 mL of fresh PBS solution was added to make up the volume. At sampling time-points of 5, 25, 48 and 73 hours, 100 mL of elution media were replaced with equal volume of fresh PBS solution. The sample was analysed by HPLC. The elution profile is illustrated in were shown in FIG. 6.

Example 14(c) Sorafinib

Figure 6:
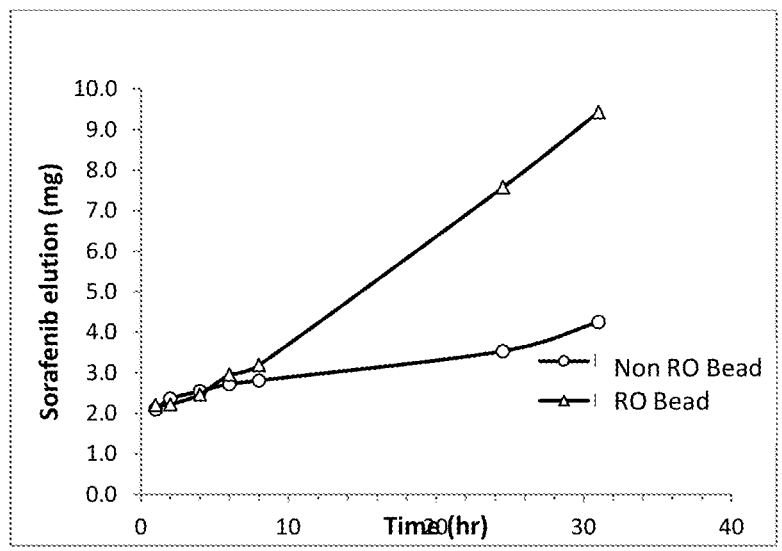
FIG. 6 shows the elution profile of RO and non RO beads loaded with sorafinib. RO beads were of size 70-150 um and had an iodine content 134 mg I/ml wet beads.

Sorafenib-loaded beads prepared according to Example 13(d) were added to 400 mL of PBS with 0.5 g/L Tween 80 in a brown jar in a 37° C. water bath. The bead suspension was stirred with a magnetic stirrer at low speed. At sampling time points of 1, 2, 4, and 6 hours, 10 mL of elution media were removed through a 5 um filter needle for HPLC analysis and 10 mL of fresh PBS solution was added to make up 400 mL volume. At sampling time-points 8, 24.5 and 31 hrs, 100 mL of elution media were replaced with equal volume of fresh PBS solution. Two replicates were run for each type of beads. The elution profiles of sorafenib from RO beads and non RO beads are shown in FIG. 6.

Example 14 (d) Vandetinib

Vandetinib loaded RO and non RO beads prepared according to Example 13(e) (2 ml beads at 30 mg vandetinib/ml beads, beads 70-150 um and RO beads having 141 mg I/ml wet beads) were placed in Amber jars containing 500 mL of PBS with magnetic flea, at ambient temperature. At each sampling time-point, the complete PBS elution medium was removed from the jar through a cannula filter by a peristaltic pump, and replaced with the same volume of fresh PBS. 5 ul of the elution medium was analysed by Cis reverse phase HPLC with detection at 254 nm. The elution profile is illustrated in FIG. 7

Example 14(e) Miriplatin

Miriplatin-loaded beads made according to Example 13(f) were added to 50 mL of PBS with 1% of Tween 80 in 100 mL Duran® bottles. The bottles were suspended in a 37° C. water bath and rotated at 75 rpm to agitate the beads. At sampling time points of 1, 5, 11, 15 and 22 days, 20 mL of elution medium was removed for ICP analysis and 20 mL of fresh PBS/Tween solution was added to make up 50 mL volume. The elution profiles of miriplatin from RO beads and non RO beads are shown in FIG. 8.

Example 14(f) Irinotecan

A sample of beads prepared in example 13(g) 163 m I/ml were added to 500 ml of PBS, in a brown jar at 37° C. and stirred with a magnetic stirrer at low speed. At sampling time points, 1 ml of elution media were removed through a 5 um filter needle and analysed by UV at 369 nm against a standard. The elution profiles were shown in FIG. 9.

Example 15. Synthesis of a Radiopaque Biodegradable PVA Microsphere

A sample of 45% Bis(acryloyl)L-Cytine—PVA beads was prepared according to Example 8 of WO2012/101455. These beads were rendered radiopaque using the protocol of Example 5 with the following specific conditions. 1 gm of dried beads, 35 mls of DMSO, 2.2 mls of methansulphonic acid, 0.4 equivalents of aldehyde prepared according to example 1 (2.22 g). The reaction was heated to 40 C for 1 hr then to 60 C for 1 hr followed by reducing the temperature to 50 C for the remainder of a 26 hr period. The iodine level obtained was 289 mg Iodine per mL of beads.

Example 16 Radiopacity of Drug-Loaded Radiopaque Beads

An aliquot of the doxorubicin loaded beads prepared according to Example 13 were subjected to microCT analysis in the same way as described in Example 12. The drug-loaded beads were found to be radiopaque. The average bead radio-opacity (Grey Scale) was determined to be 139 (n=3).

Example 17 Freeze Drying Protocol

Microspheres of the invention, whether drug loaded or non-drug loaded, may be freeze dried according to the protocol described in WO07/147902 (page 15) using an Epsilon 1-6D freeze dryer (Martin Christ Gefriertrocknungsanlagen GmbH, Osterode am Harz, Germany) with Lyo Screen Control (LSC) panel and Pfeiffer DUO 10 Rotary Vane Vacuum pump and controlled by Lyolog LL-1 documentation software, as briefly described below.

The microspheres are lyophilised by freezing at about −30° C. without a vacuum, for at least 1 h, then reducing the pressure gradually over a period of about half an hour to a pressure of in the range 0.35-0.40 mbar, while allowing the temperature to rise to about −20° C. The temperature and pressure conditions are held overnight, followed by raising the temperature to room temperature for a period of about 1-2 hours at the same time pressure, followed by a period at room temperature with the pressure reduced to about 0.05 mbar, to a total cycle time of 24 hours.

If preparations are required to be maintained under reduced pressure, at the end of the cycle and substantially without allowing ingress of air the vials are stoppered under vacuum by turning the vial closing mechanism that lowers the shelves to stopper the vials on the shelf beneath. The chamber is then aerated to allow the chamber to reach atmospheric pressure. The shelves are then returned to their original position and the chamber opened. If the samples are not maintained under reduced pressure, then the pressure is gradually returned to atmospheric before stoppering.

Example 18: In Vivo Embolisation Study

Male domestic Yorkshire crossbred swine (approximately 14 weeks old) were used in the study.

After induction of anesthesia, a sheath was placed in the femoral artery and, under fluoroscopic guidance, a guide wire was passed through the introducer and moved through to the aorta. A guide catheter, passed over the guide wire, was then placed at the entrance to the coeliac artery. The guide wire was removed, and contrast medium used to visualize the branches of the coeliac artery.

A micro-wire/micro-catheter combination was passed through the guide catheter and used to select the common hepatic artery, isolating 25 to 50% of the liver volume. A micro-catheter was passed over the guide wire into the liver lobe, the guide wire was removed and contrast medium used to capture an angiogram of the lobe. Digital subtraction angiography was performed to confirm the catheter position. 2 mls of RO beads, prepared according to Example 5 (size 75-150 um, iodine content 141 mg I/ml) was transferred to a 20 to 30 mL syringe and the packing solution discarded. A smaller syringe holding 5 mL of non-ionic contrast medium (Visipaque® 320) was connected to the larger syringe via a three-way stopcock and the beads mixed with the contrast by passage through the stopcock. The total volume was adjusted to 20 mL by addition of contrast. This suspension was administered slowly under fluoroscopic guidance, until near stasis was achieved. The volume of suspension delivered to achieve stasis was between 2 and 6 mls.

Abdominal CT images were taken pre-dose, 1 and 24 hours post dose, and on Days 7 and 14. On Day 14, a baseline CT image was taken and 75 cc of contrast material was injected. Post-contrast material injection, a second CT image was taken. The images were analyzed for the extent of visibility of beads in the liver.

The RO beads were visible on X-ray during the procedure and on CT. This was best shown on the 7 and 14 day CT scans, obtained without IV contrast (see FIG. 11). The beads were easily visible in multiple branches of the hepatic arteries. The beads were more attenuating than, and can be differentiated from, IV contrast.

The invention claimed is:

1. A method of treatment in which a hydrogel is administered into a blood vessel of a patient to embolize said blood vessel, the hydrogel being in the form of microspheres comprising a cross-linked polymer network that comprises polyvinyl alcohol (PVA) or a copolymer of PVA and a radiopaque species comprising one or more covalently bound iodines that are coupled to the PVA or copolymer of PVA through a cyclic acetal group and that provides the microspheres with greater than 15 mg of iodine per ml of microspheres fully hydrated in normal saline as a packed volume wherein the radiopaque species comprises an iodinated aromatic group.

2. The method of claim 1, wherein the blood vessel is associated with a solid tumor.

3. The method of claim 2, wherein the solid tumor is hepatocellular carcinoma.

4. A method of treatment in which a composition is administered into a blood vessel of a patient to embolize said blood vessel, the composition comprising (a) hydrogel in the form of microspheres comprising a cross-linked polymer network that comprises polyvinyl alcohol (PVA) or a copolymer of PVA and a radiopaque species comprising one or more covalently bound iodines that are coupled to the PVA or copolymer of PVA through a cyclic acetal group and that provides the microspheres with greater than 15 mg of iodine per ml of microspheres fully hydrated in normal saline as a packed volume and (b) a therapeutic agent, wherein the therapeutic agent is absorbed into the microspheres wherein the radiopaque species comprises an iodinated aromatic group.

5. The method of claim 4, wherein the blood vessel is associated with a solid tumor.

6. The method of claim 1, wherein the radiopaque species provides the microspheres with greater than 50 mg of iodine per ml of microspheres fully hydrated in normal saline as a packed volume.

7. The method of claim 1, wherein the radiopaque species provides the microspheres with greater than 100 mg of iodine per ml of microspheres fully hydrated in normal saline as a packed volume.

8. The method of claim 1, wherein the hydrogel has a net charge at physiological pH.

9. The method of claim 1, wherein the radiopaque species comprises an iodinated phenyl group.

10. The method of claim 1, wherein the microspheres have a mean diameter size range of from 10 to 2000 m.

11. The method of claim 1, wherein the microspheres have a mean radiopacity of 500HU or greater.

12. The method of claim 4, wherein the microspheres have a mean diameter size range of from 10 to 2000 µm.

13. The method of claim 4, wherein the microspheres have a mean radiopacity of 500HU or greater.

14. The method of claim 4, wherein the hydrogel has a net charge at physiological pH.

15. The method of claim 14, wherein the therapeutic agent is electrostatically held in the hydrogel and elutes from the hydrogel in electrolytic media.

16. The method of claim 4, wherein the radiopaque species provides the microspheres with greater than 50 mg of iodine per ml of microspheres fully hydrated in normal saline as a packed volume.

17. The method of claim 4, wherein the radiopaque species provides the microspheres with greater than 100 mg of iodine per ml of microspheres fully hydrated in normal saline as a packed volume.

18. A method of treatment in which a hydrogel is administered into a blood vessel of a patient to embolize said blood vessel, the hydrogel having a net charge at physiological pH in the form of microspheres having a mean diameter size range of from 10 to 2000 m and comprising a cross-linked polymer network that comprises polyvinyl alcohol (PVA) or a copolymer of PVA and a radiopaque species comprising an iodinated aromatic group that is coupled to the PVA or copolymer of PVA through a cyclic acetal group and that provides the microspheres with greater than 50 mg of iodine per ml of microspheres fully hydrated in normal saline as a packed volume.

* * * * *